(12) United States Patent
Alving et al.

(10) Patent No.: US 9,193,739 B2
(45) Date of Patent: Nov. 24, 2015

(54) INDUCTION OF HIGHLY SPECIFIC ANTIBODIES TO A HAPTEN BUT NOT TO A CARRIER PEPTIDE BY IMMUNIZATION

(71) Applicant: Walter Reed Army Institute of Research, Washington, DC (US)

(72) Inventors: Carl R. Alving, Bethesda, MD (US); Gary R. Matyas, Olney, MD (US); Arthur E. Jacobson, Potomac, MD (US); Fuying Li, Rockville, MD (US); Malliga R. Iyer, Germantown, MD (US); Kenner C. Rice, Bethesda, MD (US); Kejun Cheng, Potomac, MD (US); Alexander Mayorov, Perm (RU)

(73) Assignees: THE UNITED STATES OF AMERICA, AS REPRESENTED BY THE SECRETARY OF THE ARMY, Washington, DC (US); THE UNITED STATES OF AMERICA, AS REPRESENTED BY THE SECRETARY, DEPT OF HEALTH HUMAN SERVICES, Washington, DC (US)

( * ) Notice: Subject to any disclaimer, the term of this patent is extended or adjusted under 35 U.S.C. 154(b) by 0 days.

(21) Appl. No.: 14/377,126

(22) PCT Filed: Feb. 8, 2013

(86) PCT No.: PCT/US2013/025350
§ 371 (c)(1),
(2) Date: Aug. 6, 2014

(87) PCT Pub. No.: WO2013/119954
PCT Pub. Date: Aug. 15, 2013

(65) Prior Publication Data
US 2015/0098935 A1    Apr. 9, 2015

Related U.S. Application Data

(60) Provisional application No. 61/633,996, filed on Feb. 8, 2012.

(51) Int. Cl.
| | | |
|---|---|---|
| *A61K 31/485* | (2006.01) | |
| *C07D 489/02* | (2006.01) | |
| *C07K 16/00* | (2006.01) | |
| *C07D 497/08* | (2006.01) | |
| *A61K 47/48* | (2006.01) | |
| *C07K 16/18* | (2006.01) | |
| *A61K 39/00* | (2006.01) | |

(52) U.S. Cl.
CPC .......... *C07D 497/08* (2013.01); *A61K 47/4833* (2013.01); *C07K 16/18* (2013.01); *A61K 2039/505* (2013.01); *C07K 2317/76* (2013.01)

(58) Field of Classification Search
USPC ................... 514/282; 546/44; 530/326, 387.1
See application file for complete search history.

(56) References Cited

PUBLICATIONS

Stowe, G.N. et al.: A vaccine strategy that induces protective immunity against heroin. J. Med. Chem., vol. 54, pp. 5195-5204, 2011.*

* cited by examiner

*Primary Examiner* — Charanjit Aulakh
(74) *Attorney, Agent, or Firm* — Elizabeth Arwine; Sana A. Pratt

(57) ABSTRACT

In this application is described a composition and method for inducing in a subject anti-hapten antibodies without inducing antibodies to the carrier protein. Kits for designing and making compositions with desired haptens are also described.

35 Claims, 7 Drawing Sheets

SEQUENCE LISTING

```
<160> NUMBER OF SEQ ID NOS: 3

<210> SEQ ID NO 1
<211> LENGTH: 23
<212> TYPE: PRT
<213> ORGANISM: Artificial sequence
<220> FEATURE:
<223> OTHER INFORMATION: MPER 23-amino acid sequence

<400> SEQUENCE: 1

Leu Glu Leu Asp Lys Trp Ala Ser Leu Trp Asn Trp Phe Asn Ile
1               5                   10                  15

Thr Asn Trp Leu Trp Tyr Ile Lys
                20

<210> SEQ ID NO 2
<211> LENGTH: 15
<212> TYPE: PRT
<213> ORGANISM: Artificial sequence
<220> FEATURE:
<223> OTHER INFORMATION: derived from universal T cell epitope from
      Tetanus toxin

<400> SEQUENCE: 2

Gln Tyr Ile Lys Ala Arg Ser Lys Phe Ile Gly Ile Thr Glu Leu
1               5                   10                  15

<210> SEQ ID NO 3
<211> LENGTH: 15
<212> TYPE: PRT
<213> ORGANISM: Artificial sequence
<220> FEATURE:
<223> OTHER INFORMATION: universal T cell epitope from Tetanus toxin

<400> SEQUENCE: 3

Gln Tyr Ile Lys Ala Asp Ser Lys Phe Ile Gly Ile Thr Glu Leu
1               5                   10                  15
```

INDUCTION OF HIGHLY SPECIFIC ANTIBODIES TO A HAPTEN BUT NOT TO A CARRIER PEPTIDE BY IMMUNIZATION

This application claims benefit of priority under 35 U. S. C. 119 (e) from U.S. Application Ser. No. 61/633,996 filed on Feb. 8, 2012, herein incorporated by reference in its entirety.

INTRODUCTION

Haptens are defined as molecules, generally small molecules, that do not induce antibodies in animals or humans by themselves. As originally defined by Landsteiner, to induce antibodies it is necessary to attach the hapten to a carrier molecule, such as a carrier protein (Butler V P Jr, Beiser S M, 1973, Adv. Immunol. 17, 255-310). One characteristic of the carrier to which the hapten is attached is that the carrier-hapten conjugate stimulates antibodies that react both with the carrier and with the hapten (Berzofsky & Berkower, Chapter 19, in Fundamental Immunology, Edited by William E. Paul, 4th Edition, 1998). The immunization procedure may result in independent antibodies that react independently to the carrier and to the hapten-carrier complex. However, antibodies induced by hapten-carrier conjugates are heterogeneous in that the antibodies may have partial simultaneous specificity both to the hapten and to adjacent peptide molecules that are present in the carrier close to the attachment point of the hapten (Singer S J, 1964, Immunochemistry 1, 15-20). The heterogeneity of the antibody binding specificity that includes the carrier itself can be a problem that can lead to induction of a dominant antibody specificity to the carrier that actually interferes with the subsequent induction of antibodies to the hapten (Dagan et al., 2010, Vaccine 28, 5513-5523). Thus, if antibodies exist to the carrier, then subsequent immunization with the carrier-hapten complex would interfere with the induction of antibodies to the hapten. This is based on the fundamental principle, defined herein as immune interference, that B cells that recognize the carrier alone would produce antibodies that sterically block binding of the carrier-hapten to the B cells that would recognize both hapten and carrier.

What is needed is a hapten-carrier complex that induces antibodies that recognize the hapten but does not induce antibodies that recognize the peptide carrier. The present invention addresses this and other unfulfilled needs in the art.

SUMMARY OF THE INVENTION

In this application is disclosed a synthetic liposome composition comprising liposomes (L) containing monophosphoryl lipid A (MPLA) [L(MPLA)] and an immunoconjugate comprising a carrier and a hapten. In one embodiment, the carrier is a 23 amino acid hydrophobic membrane proximal external region peptide (MPER) derived from the gp41 transmembrane protein of HIV-1 that spontaneously associates with the outer surface of bilayers of liposomes containing MPLA during liposome formation. When a peptide-heroin analog hapten is conjugated to the MPER on the liposome, and the liposomes are used for immunization, surprisingly, antibodies to the heroin hapten are induced in the subject but no antibodies are induced to the MPER peptide carrier. However, the liposomes containing MPLA and MPER, but lacking the peptide-heroin analog hapten, readily induce antibodies to the MPER. Thus, the MPER to which the heroin hapten was conjugated induced anti-heroin analog antibodies without inducing antibodies to the MPER.

The benefit of this unexpected result is two-fold: first, immune interference caused by antibodies to the peptide carrier is not produced that would be expected to inhibit subsequent antibody responses when the same carrier is used for immunization against the same or any different hapten. Second, antibodies to the HIV-1 peptide itself may be important for diagnostic assays to HIV-1, and if such antibodies were induced in a person not infected with HIV-1, then the immunization with the HIV-1 peptide-hapten might be expected to induce false positive diagnostic HIV-1 assays.

Therefore, it is one object of the present invention to provide a liposome-hapten composition comprising a formulation of liposomes of the present invention comprising L(MPLA), and at least one immunoconjugate comprising a carrier peptide and at least one hapten, such that when the composition is administered to a subject, anti-hapten antibodies are induced in the subject without inducing interference antibodies. In one aspect, the immunoconjugate is part of the liposome, for example, embedded or semi-embedded into the liposome as described in the Examples below for a hydrophobic membrane proximal external region peptide (MPER) derived from the gp41 transmembrane protein of HIV-1. When a hapten is conjugated to the carrier MPER, a liposome-hapten composition is formed.

Alternatively, the immunoconjugate is a carrier peptide or protein which is not part of the L(MPLA), i.e. not embedded in the liposome The carrier could be bound to the surface of the liposomes or be covalently attached to the liposomes. An anchor such as a lipid could be attached to the carrier with the anchor embedded in the lipid bilayer of the liposomes, thus attaching it to the surface. The commonly used examples are fatty acids, such as palmatic acid, and phosphatidylethanolamine (White et al., 1995, Vaccine 13, 1111-1122; Knoll et al., 2000, Rev. in Mol. Biotech. 74, 137-158; Wang et al., 2005, J. Biol. Chem. 280, 22839-33846). Alternatively, the hapten-carrier complex is encapsulated in the aqueous center of the liposome. See Matyas et al., 2003 Meth. Enzymol 373:34.

In one aspect the immunoconjugate is free, i.e. not associated or attached to the liposome. When one or more haptens are conjugated to the carrier peptide or protein and mixed with the L(MPLA) a liposome-hapten composition is produced, as shown in the Examples for the immunoconjugate comprising the tetanus toxoid (TT) and a hapten. Administration of the composition of the invention to a subject results in induction of a potent immune response to the haptens. In one embodiment, one or more HIV peptide is attached or associated with the carrier peptide, for example, an HIV protein or HIV peptides are attached or associated with the carrier protein and administered along with the free carrier-hapten immunoconjugate. Some examples of HIV proteins which could be used include, gp120, gp41, gp140, gp145, modifications of gp140 and gp145 such that the gp 120 is not cleaved from the gp41 and the gp41 is truncated to allow solubility of the protein. These HIV proteins can be derived from different virus strains or from different stages in the infection process. Examples of HIV peptides or HIV peptide analogs include a 24-amino acid MPER described in this application, an extended 48-amino acid MPER (Karasavvas et al., 2008, Biochem. Biophys. Res. Commun. 366, 982-987; Beck et al., 2008, J. Drug Target. 16, 535-542), from gp120: the V2 loop, V3 loop, or the V/v2 loop, and the drug T20. The peptides can be derived from various strains of HIV and at various stages in the infection process.

It is yet another object of the present invention to provide novel haptens and compositions comprising novel haptens. Heroin haptens 3-8 as represented in FIG. 1 are novel, and can be used in the liposome-hapten compositions of the present invention, or in another composition for detection of heroin in a sample. The novel haptens of the present invention are as follows:

Hapten 3: N-((4R,4aR,7R,7aR,12bS)-9-hydroxy-3-methyl-2,3,4,4a,7,7a-hexahydro-1H-4,12-methanobenzofuro[3,2-e]isoquinolin-7-yl)-3-mercaptopropanamide Hapten 4: (4R,4aR,7S,7aR,12bS)-9-(3-mercaptopropanamido)-3-methyl-2,3,4,4a,5,6,7,7a-octahydro-1H-4,12-methanobenzofuro[3,2-e]isoquinolin-7-yl acetate Hapten 5: N,N'-((4R,4aR,7S,7aR,12bS)-3-(4-(3-mercaptopropanamido)butyl)-2,3,4,4a,5,6,7,7a-octahydro-1H-4,12-methanobenzofuro[3,2-e]isoquinoline-7,9-diyl)diacetamide Hapten 6: N-((4R,4aR,7S,7aR,12bS)-7-acetamido-3-methyl-2,3,4,4a,5,6,7,7a-octahydro-1H-4,12-methanobenzofuro[3,2-e]isoquinolin-9-yl)-3-mercaptopropanamide Hapten 7: 3-mercapto-N-((4R,4aR,7R,7aS,12bS)-3-methyl-7-(2-oxopropyl)-2,3,4,4a,5,6,7,7a-octahydro-1H-4,12-methanobenzofuro[3,2-e]isoquinolin-9-yl)propanamide Hapten 8: N-(4-((4R,4aR,7R,7aS,12bS)-7,9-bis(2-oxopropyl)-4,4a,5,6,7,7a-hexahydro-1H-4,12-methanobenzofuro[3,2-e]isoquinolin-3(2H)-yl)butyl)-3-mercaptopropanamide It is another object of the present invention to provide a method for inducing in a subject anti-hapten antibodies without inducing antibodies to the peptide carrier. The method includes administering the liposome-hapten composition of the present invention wherein the desired hapten, or haptens, is attached, conjugated, or crosslinked to the carrier peptide in an amount sufficient to produce the anti-hapten antibodies in the subject. It is envisioned that a variety of liposomes can be administered each with one or multiple carrier peptide, the carrier peptide being the same or different on each liposome, each carrier peptide having one or multiple, similar or different haptens, which are specific for the same or multiple antigens or drugs.

It is yet another object of the present invention to provide a method for producing antibodies to one or more hapten by administering a liposome formulation of the present invention to a subject, such that antibodies to the hapten(s) are produced. The antibodies can optionally be isolated for use in other assays. As stated above liposomes can have the immunoconjugate encapsulated, incorporated in the lipid bilayer, anchored in the lipid bilayer, attached to the surface or simply be mixed with liposomes.

It is another object of the present invention to provide an immunogenic composition as a therapeutic or prophylactic composition for treatment of a subject with a specific drug addiction or recovering from a specific drug addiction. The composition comprises one or more liposome-hapten of the present invention wherein the hapten is from the drug of abuse, including but not limited to, heroin, morphine, methamphetamine, cocaine, and nicotine.

It is another object of the present invention to provide a vaccine composition comprising the liposome-hapten composition of the present invention such that protection from intoxication with a drug, drug addiction, infection with an infectious organism, or severity of ailment or undesired condition is prevented or ameliorated by administering the vaccine. The vaccine comprises liposome-hapten formulations of the present invention which are able to induce anti-hapten antibodies in the subject. Since there is no immunological interference due to administration of the liposome/hapten formulations of the present invention, multiple liposomes with varied haptens, or multiple carrier proteins on the same liposome, each having at least one hapten, for example for use as a multivalent vaccine, can be administered, together or individually, serially or in one dose, thereby facilitating vaccination protocols.

In yet another embodiment, the present invention provides a kit comprising one or more carrier proteins or peptides for constructing an immunoconjugate with a desired hapten. The kit can optionally also provide liposome formulations comprising L(MPLA), and/or reagents for forming the liposomes L(MPLA) with a carrier protein or peptide with the desired hapten embedded in, attached to, associated with, or encapsulated by the liposome. The kit can be provided with ancillary agents useful for generating a desired liposome-hapten composition. The kit is useful for making a liposome-hapten composition for use in a desired treatment, vaccination, therapy, or diagnostic assay.

BRIEF DESCRIPTION OF THE DRAWINGS

FIG. 4. Serum IgG responses to MPER and MPER carrier 9 weeks after primary immunization. Mice were immunized with L(MPLA+HerHap-PEG-MPER carrier) (A, C) or L(MPLA+MPER carrier) (B, D), at weeks 0, 3 and 6. Each curve represents an individual mouse (5 mice/liposome formulation). Values represent the mean±standard deviation of triplicate determinations.

DETAILED DESCRIPTION

Figure 1:
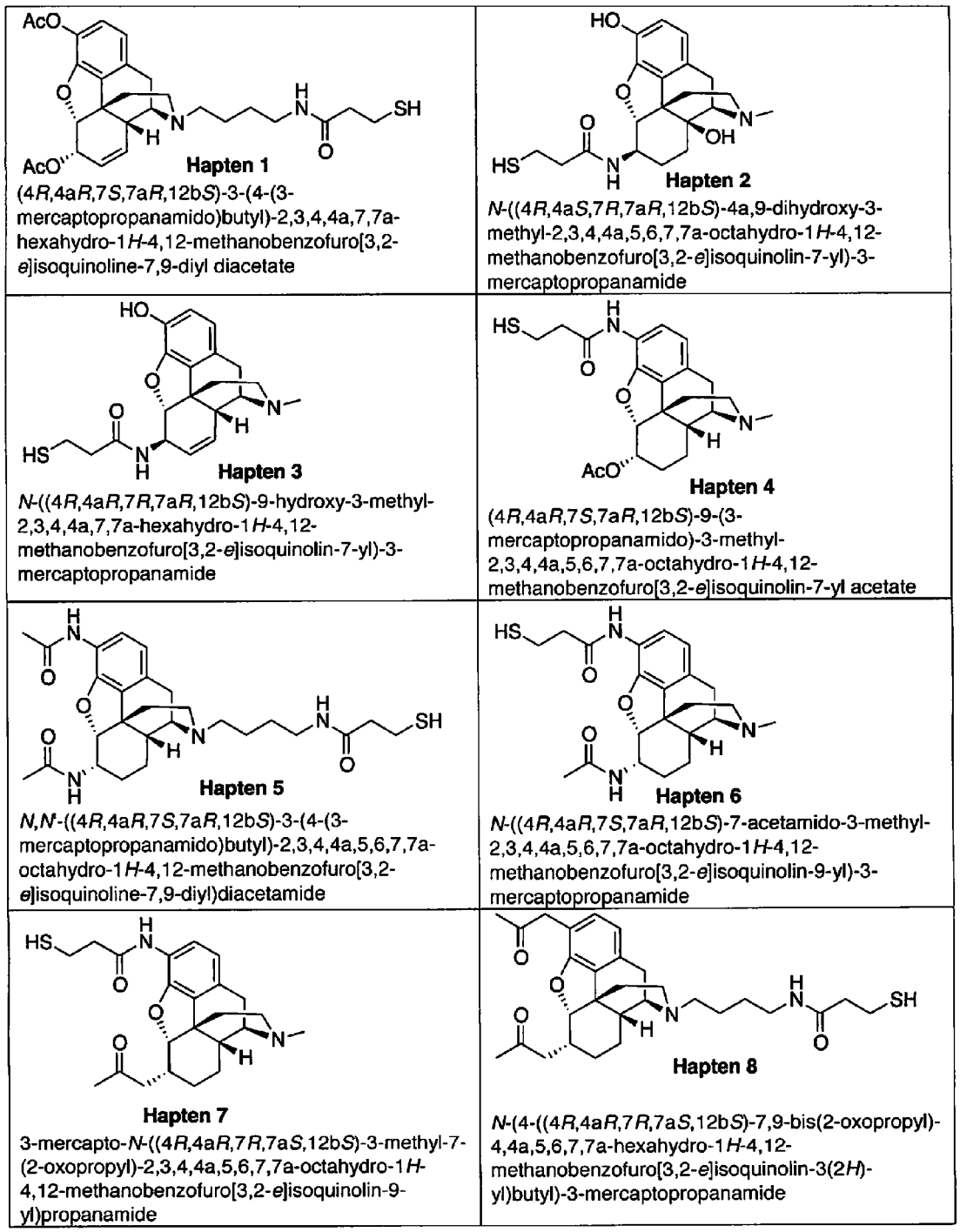
FIG. 1. Chemical structures of some heroin haptens of the invention.

In the description that follows, a number of terms are extensively utilized. In order to provide a clearer and consistent understanding of the specification and claims, including the scope to be given such terms, the following definitions are provided.

Subject. Includes human, animal, avian, e.g., horse, donkey, pig, mouse, rat, hamster, monkey, chicken.

Hapten. Peptides and other small molecules, analogs, and modified versions thereof, which are used as antigens are referred to as haptens. They are able to act as recognition sites for production of specific antibodies but cannot by themselves stimulate the necessary immune response. Haptens can be made immunogenic by coupling them to a suitable carrier molecule such as a protein, which can be processed by antigen presenting cells and presented to the immune system such that the immune system recognizes the unmodified small molecule. Further, the hapten is characterized as the specificity-determining portion of the hapten-carrier conjugate, that is, it is capable of reacting with an antibody specific to the hapten in its free state.

Crosslinker. A moiety which has a chemical functionality suitable for attachment of the haptenic moiety to a spacer moiety or carrier.

Spacer. A chemical moiety that provides a molecular distance between the hapten and the carrier.

Liposomes

In one embodiment, the present invention provides a formulation of liposomes containing lipid A or monophophoryl lipid A (MPLA). Liposomes are closed bilayer membranes containing an entrapped aqueous volume. Liposomes may also be unilamellar vesicles possessing a single membrane bilayer or multilamellar vesicles with multiple membrane bilayers, each separated from the next by an aqueous layer. The structure of the resulting membrane bilayer is such that the hydrophobic (non-polar) tails of the lipid are oriented toward the center of the bilayer while the hydrophilic (polar) heads orient towards the aqueous phase. Suitable hydrophilic polymers for surrounding the liposomes include, without limitation, PEG, polyvinylpyrrolidone, polyvinylmethylether, polymethyloxazoline, polyethyloxazoline, polyhydroxypropyloxazoline, polyhydroxypropylmethacrylamide, polymethacrylamide, polydimethylacrylamide, polyhydroxypropylmethacrylate, polyhydroxethylacrylate, hydroxymethylcellulose hydroxyethylcellulose, polyethyleneglycol, polyaspartamide and hydrophilic peptide sequences as described in U.S. Pat. Nos. 6,316,024; 6,126,966; 6,056,973; 6,043,094, the contents of which are incorporated by reference in their entirety. Liposomes can be made without hydrophilic polymers, as exemplified in the Examples below. Therefore liposome formulations with or without hydrophilic polymers are part of this invention.

Liposomes may be comprised of any lipid or lipid combination known in the art. For example, the vesicle-forming lipids may be naturally-occurring or synthetic lipids, including phospholipids, such as phosphatidylcholine, phosphatidylethanolamine, phosphatidic acid, phosphatidylserine, phasphatidylglycerol, phosphatidylinositol, and sphingomyelin as disclosed in U.S. Pat. Nos. 6,056,973 and 5,874,104. The vesicle-forming lipids may also be glycolipids, cerebrosides, or cationic lipids, such as 1,2-dioleyloxy-3-(trimethylamino)propane (DOTAP); N-[1-(2,3,-ditetradecyloxy)propyl]-N,N-dimethyl-N-hydroxyethylammonium bromide (DMRIE); N-[1[(2,3,-dioleyloxy)propyl]-N,N-dimethyl-N-hydroxy ethylammonium bromide (DORIE); N-[1-(2,3-dioleyloxyl)propyl]-N,N,N-trimethylammonium chloride (DOTMA); 3 [N—(N',N'-dimethylaminoethane) carbamoly] cholesterol (DC-Chol); or dimethyldioctadecylammonium (DDAB) also as disclosed in U.S. Pat. No. 6,056,973. Cholesterol may also be present in the proper range to impart stability to the vesicle as disclosed in U.S. Pat. Nos. 5,916,588 and 5,874,104.

Additional liposomal technologies are described in U.S. Pat. Nos. 6,759,057; 6,406,713; 6,352,716; 6,316,024; 6,294,191; 6,126,966; 6,056,973; 6,043,094; 5,965,156; 5,916,588; 5,874,104; 5,215,680; and 4,684,479, the contents of which are incorporated herein by reference. These describe liposomes and lipid-coated microbubbles, and methods for their manufacture. Thus, one skilled in the art, considering both the disclosure of this invention and the disclosures of these other patents could produce a liposome for the purposes of the present invention.

Preferably, the liposome includes monophosphoryl Lipid A (MPLA). MPLA by itself is toxic to humans and animals. However, when present in liposomes the toxicity is abolished. Procedures for preparation of the liposomes with MPLA are described herein and in Alving et al., 2012, Expert Rev Vaccines 11, 733-7440). MPLA serves as a potent adjuvant and serves to raise the immunogenicity of the liposome and peptides, proteins or haptens associated with the liposome. Many other compounds can be used to render liposomes immunogenic, however, care must be taken to insure potency and safety.

Haptens

A hapten is a small molecule that can elicit an immune response only when attached to a carrier. Heroin and its metabolites are small molecules which need to be attached or associated with a larger carrier molecule in order to elicit an immune response. The present inventors have designed and synthesized heroin derivative haptens which have structural and stereochemical features of heroin such that when a hapten is conjugated to a carrier to produce a hapten-carrier immunoconjugate, the immunoconjugate is effective in generating an antibody immune response to the hapten but not to the carrier molecule. This was shown with immunoconjugates having different carrier molecules.

Haptens in accordance with the present invention, some of which are presented in FIG. 1, may be synthesized de novo or from a heroin-related compound. In some embodiments, heroin or a heroin derivative compound is employed as the starting material in synthesis of the haptens. In another embodiment, haptens can be designed to mimic heroin a molecular feature of heroin. In other embodiments, the heroin haptens can be generated by de novo synthesis in accordance with standard chemical methods well known in the art. (Stowe et al., 2011 CNS Neurological Disorders-Drug Targets 10:865-875). Basically, by studying the structure of the compound and the functional groups, such as amines, hydroxyls, carboxyls, ketones etc., a hapten structure can be designed and made attachable to a carrier.

Heroin haptens 3-8 as represented in FIG. 1 are novel, and can be used in the immunoconjugate compositions of the present invention. Additionally, since the haptens are the specificity determining portion of the immunoconjugate, they can react with antibodies directed to the immunoconjugate and therefore useful for detection of heroin in a sample.

The novel haptens of the present invention are as follows:

Hapten 3: N-((4R,4aR,7R,7aR,12bS)-9-hydroxy-3-methyl-2,3,4,4a,7,7a-hexahydro-1H-4,12-methanobenzofuro[3,2-e]isoquinolin-7-yl)-3-mercaptopropanamide Hapten 4: (4R,4aR,7S,7aR,12bS)-9-(3-mercaptopropanamido)-3-methyl-2,3,4,4a,5,6,7,7a-octahydro-1H-4,12-methanobenzofuro[3,2-e]isoquinolin-7-yl acetate Hapten 5: N,N'-((4R,4aR,7S,7aR,12bS)-3-(4-(3-mercaptopropanamido)butyl)-2,3,4,4a,5,6,7,7a-octahydro-1H-4,12-methanobenzofuro[3,2-e]isoquinoline-7,9-diyl)diacetamide Hapten 6: N-((4R,4aR,7S,7aR,12bS)-7-acetamido-3-methyl-2,3,4,4a,5,6,7,7a-octahydro-1H-4,12-methanobenzofuro[3,2-e]isoquinolin-9-yl)-3-mercaptopropanamide Hapten 7: 3-mercapto-N-((4R,4aR,7R,7aS,12bS)-3-methyl-7-(2-oxopropyl)-2,3,4,4a,5,6,7,7a-octahydro-1H-4,12-methanobenzofuro[3,2-e]isoquinolin-9-yl)propanamide Hapten 8: N-(4-((4R,4aR,7R,7aS,12bS)-7,9-bis(2-oxopropyl)-4,4a,5,6,7,7a-hexahydro-1H-4,12-methanobenzofuro[3,2-e]isoquinolin-3(2H)-yl)butyl)-3-mercaptopropanamide These haptens were designed to have a chemical structure that was expected to produce antibodies that recognize heroin. Heroin has 3 groups which can be relatively easily modified. They are the acetyl groups at the 3 and 6 positions and the N at position 17. The acetyl groups are very liable. Some of the haptens were designed with the acetyls replaced by stable substitutions that mimic the structure of the acetyl group.

The above listed haptens and other haptens with an opiate in the morphine-acetylmorphine-heroin-oxymorphone-oxycontin family with functionality that enables it to conjugate with a variable linker at either the C3 or C6 or N-position in the molecule is part of this invention. As is evident to a person with ordinary skill in the art, the sulfhydryl group can be substituted for other functional groups including, but not limited to, amines, carboxyls, aldehydes, and ketones. Also the length from the NH to the functional coupling group can be altered without affecting the core antigenic structure. In some embodiments, the carrier moiety can be modified with a derivatizing molecule or spacer molecule in order to generate a functional group for reacting with the heroin hapten. These methods are well-known in the art.

Carrier Moiety

The haptens are covalently or non-covalently conjugated to a carrier moiety, using conventional methods known in the art, thus producing a hapten-carrier immunoconjugate. A "carrier moiety," as used herein, refers to a conjugation partner capable of enhancing the immunogenicity of a hapten. For instance, polymers can be used, e.g. carbohydrates such as dextran, mannose or mannan. Integral membrane proteins from, e.g., *E. coli* and other bacteria are also useful conjugation partners. Suitable carriers are typically large, slowly metabolized macromolecules such as proteins; polysaccharides (such as latex functionalized SEPHAROSE™, agarose, cellulose, cellulose beads and the like); polymeric amino acids (such as polyglutamic acid, polylysine, and the like); amino acid copolymers; and inactive virus particles or attenuated bacteria, such as *Salmonella*. Especially useful carrier proteins are serum albumins, edestin, keyhole limpet hemocyanin (KLH), sheep red blood cells, certain immunoglobulin molecules, thyroglobulin, human serum albumin, ovalbumin, bovine serum albumin (BSA), tetanus toxoid (TT), and diphtheria toxoid (CRM), D-lysine, D-glutamic acid, members of the LTB family of bacterial toxins, recombinant pox virus subunits, retrovirus nucleoprotein, vesicular stomatitis virus nucleocapsid protein, and rabies ribonucleoprotein.

In a specific embodiment, the carrier peptide is MPER. MPER is an amino acid sequence of the membrane proximal external region (MPER) of HIV-1 gp41 protein. MPER was immunogenic when used in liposomes containing MPLA (Matyas et al., 2009, AIDS 23, 2069-2077). Any MPER of any size and of any sequence present in the various strains of the HIV can be used. When the carrier is embedded in the liposome, the carrier peptide should be long enough to anchor the immunoconjugate complex (carrier-hapten) to the liposome surface.

In one embodiment, MPER comprises the following 23-amino acid sequence identified as SEQ ID NO:1:

Leu-Glu-Leu-Asp-Lys-Trp-Ala-Ser-Leu-Trp-Asn-Trp-

Phe-Asn-Ile-Thr-Asn-Trp-Leu-Trp-Tyr-Ile-Lys

Any of the above-listed amino acids may be replaced by a suitable unnatural amino acid, e.g. as described in Chemistry and Biochemisty of Amino Acids, Peptides and proteins, Vol. 7, ed. B. Weinstein (1983), incorporated herein by reference. Variants of the above-listed amino acid sequences are also contemplated. The variants can be prepared, for example, by synthesizing the variant, or by introducing appropriate nucleotide changes into DNA encoding the peptide.

Amino acid substitutions can be the result of replacing one amino acid with another amino acid having similar structural and/or chemical properties, such as the replacement of a leucine with a serine, i.e., conservative amino acid replacements. Insertions or deletions can optionally be in the range of about 1 to 5 amino acids. The variation allowed can be determined by systematically making insertions, deletions or substitutions of amino acids in the sequence and testing the resulting variants for activity exhibited by the source molecule. Preferably, variants have a biological activity of 23-amino acid MPER peptide.

Conjugation and Linker Moeities

In yet another embodiment, a hapten is conjugated to the carrier peptide. Methods for attaching the hapten to the carrier peptide are well known in the art, and include use of a spacer, a crosslinker, or another peptide. Such methods are described in, e.g., Harlow and Lane, Antibodies: A Laboratory Manual, Cold Spring Harbor Laboratory, Cold Spring Harbor, N.Y. (1988) and Bioconjugate Techniques, $2^{nd}$ Ed, 2008, Greg T Hermanson, Academic Press, Inc., incorporated herein by reference.

There are a large number of functional groups which can be used to facilitate the conjugation of a hapten to a protein. These include functional moieties such as carboxylic acids, anhydrides, mixed anhydrides, acyl halides, acyl azides, alkyl halides, N-maleimides, imino esters, isocyanates, amines, thiols, isothiocyanates, and others known in the art. These moieties are capable of forming a covalent bond with a reactive group of a protein. Depending upon the functional moiety used, the reactive group may be the free amino group of a lysine residue or a free thiol group of a cysteine residue on a protein which, when reacted, results in amide, amine, thioether, amidine urea, or thiourea bond formation. One of ordinary skill in the art will recognize that other suitable activating groups and conjugation techniques can be used, such as amino acids lysine, arginine, cysteine, aspartate, glutamate, tyrosine and/or histidine. In an embodiment, conjugation is to hydroxyls such as tyrosine or sugars or those described in Wong, Chemistry of Protein Conjugation and Cross-Linking (CRC Press, Inc., 1991); Hermanson, Bioconjugate Techniques (Academic Press, 1996); and Dick and Beurret, "Conjugate Vaccines," Contrib. Microbiol. Immunol., 10: 48-114 (Karger, Basal, 1989).

If the conjugation moiety is not suitable for conjugation directly with the carrier moiety, a linker moiety comprising chemical functionality suitable for conjugation with the conjugation moiety and protein moiety can be used. As is known in the art, there is a wide range of available methods for linking conjugation moieties to carrier moieties, any of which are suitably adapted for use with the invention. The length and nature of the linker moiety is such that the hapten is displaced a sufficient distance from the carrier moiety to elicit a suitable antibody response to the hapten in vivo. In one embodiment, the linker moiety comprises a N-maleoyl-γ-aminobutyric acid (MGABA) moiety. Alternative linker moieties suitable for the hapten-to-protein carrier conjugations described herein include carbonyl (such as an aldehyde or a ketone functionalities) and hydroxylamine groups, suitable for oxime-forming conjugation as described by Rose, J. Am. Chem. Soc, 1 16: 30-33 (1994). Other suitable conjugation methods include "click" ligation, which requires an azide and an alkyne linker moieties (Rodionov, et al. J. Am. Chem. Soc, 129: 12696-12704 (2007)); and a Staudinger ligation, which requires an azide and a carboxyl linker moieties (Saxon, et al. Science 287: 2007-2010 (2000)).

As is known in the art, there is a wide range of available methods for conjugating polypeptides to carrier moieties and/or linker moieties, any of which are suitably adapted for use with the invention. Most strategies involve conjugating the polypeptide to a derivatized molecule on the carrier moiety via formation of a covalent bond between reactive groups on the polypeptide and carrier. Suitably, one or more amino acids having a reactive group incorporated in the polypeptide sequence is used to link the polypeptide to the carrier moiety or linker moiety. Suitable conjugation moieties are those having amino groups, carboxyl groups or sulfhydryl groups. As will be appreciated, functional groups of amino acids in the sequence of the polypeptide haptens of the invention may be used as a conjugation moiety to couple the polypeptide haptens to the carrier moiety or linker moiety.

The hapten can be conjugated to a protein using a homo-bifunctional cross-linker, such as glutaraldehyde, DSG, BM[PEO]4, or BS3, which has functional groups reactive towards amine groups or carboxyl groups of a protein.

Several hetero-bifunctional cross-linkers are known in the art. For example, the hetero-bifunctional cross-linker can contain a functional group which reacts with the free amino group of lysine residues of a protein, and a functional group which reacts with a cysteine residue or sulfhydryl group present on the antigen, thereby leading to the formation of a thioether linkage. The cysteine residue or sulfhydryl group can be naturally present on the antigen, made available for reaction by reduction, or engineered or attached on the hapten and optionally made available for reaction by reduction. Several such hetero-bifunctional cross-linkers are known in the art, and include, for example, SMPH, Sulfo-MBS, Sulfo-EMCS, Sulfo-GMBS, Sulfo-SIAB, Sulfo-SMPB, Sulfo-SMCC, SVSB, and SIA, which are commercially available from, for example, Pierce Thermo Fisher Scientific (Rockford, Ill., USA).

For example, the hapten can be attached to the carrier peptide in the form of the following sequence:

A-B-C-D-E-F wherein, A, B, C, D, E and F are defined as follows:
A is the hapten
B is a crosslinker
C is a spacer
D is a peptide sequence
E is a spacer similar or different than the spacer in C above.
F is the carrier protein, for example, the hydrophobic MPER identified in SEQ ID NO:1.

Spacer Moieties

The spacer moieties (C) of the present invention comprise a sequence of 1 to about 5 amino acids comprising one or more polyethylene glycol (PEG) units. PEG is a polymer of ethylene oxide and ethylene glycol. There can be well more than 5 and it could be branched. PEG is a useful spacer moiety because of its specific properties, i.e. water solubility, high mobility in solution, lack of toxicity and immunogenicity, ready clearance from the body and altered distribution in the body. Any spacer could be used, but the hydrophilic spacer PEG was chosen to keep the hapten away from the lipid bilayer and not to allow the hapten to partition in the bilayer. The optimal length of spacers can be determined by a person with skill in the art by trial and error.

The spacer moiety comprises 1 to about 5 consecutive PEG spacers, the spacer length being from 1 to about 40 PEG units with the total number of PEG units in the spacer moiety not exceeding 40. The PEG units can be linear, branched, or multiply branched. The PEGylation reagents can contain different lengths of PEG units, such as for example, 4 units, 8 units, 12 units, 24 units, 30 units and the like. The PEG unit can be defined by the following structure:

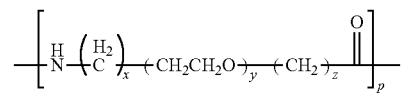

wherein x is between 0 and 1 inclusive, y is between 0 and 10 inclusive, and z is between 1 and 10 inclusive, p is between 1 and 3 inclusive, and p*(x+y+z) is less than 40. In an embodiment, the spacer moiety comprises about 1 to about 40 PEG units. In another embodiment, the spacer moiety comprises about 1 to about 4 PEG units, about 1 to about 8 PEG units, about 1 to about 12 PEG units, about 1 to about 24 PEG units, or about 1 to about 30 PEG units.

In an embodiment, y is between 1 and about 30 inclusive. In an embodiment, y is between about 1 to about 24 inclusive. In an embodiment, y is between 1 and about 12 inclusive. In yet another embodiment, y is between 1 to about 8 inclusive. In an embodiment, x is between 0 and 1, y is between 1 and 8, z is between 1 and 3 and p is between 1 and 5.

The spacer moieties of the invention can be made by a process known as PEGylation, where ethylene glycol or ethylene oxide polymer units are chemically coupled to the amino acid subsequence. The process of PEGylation is known to those of skill in the art, and is described in detail in, for example, The Handbook of Pharmaceutical Biotechnology, S. Cox ed., Wiley (2007). The first step of the PEGylation is the suitable functionalization of the PEG polymer at one or both terminals. PEGs that are activated at each terminus with the same reactive moiety are known as "homobifunctional", where as if the functional groups present are different, then the PEG derivative is referred as "heterobifunctional" or "heterofunctional." The chemically active or activated derivatives of the PEG polymer are prepared to attach the PEG to the desired molecule. The choice of the suitable functional group for the PEG derivative is based on the type of available reactive group on the molecule that will be coupled to the PEG. Reagents used for PEGylation of proteins can include linear or branched PEG, with amine-reactive or sulfhydryl-reactive groups. These include, for example, lysine, cysteine, histidine, arginine, aspartic acid, glutamic acid, serine, threonine, tyrosine. The N-terminal amino group and the C-terminal carboxylic acid can also be used. The PEGylation reagents can contain different lengths of PEG units, such as for example, 4 units, 8 units, 12 units, 24 units, 30 units and the like.

A $(PEG)_2$ spacer was used with the TT-hapten immunoconjugate in order to keep the hapten close to the TT. $(PEG)_4$ was chosen for the MPER-hapten to move the hapten away from the lipid bilayer to prevent the hapten from partitioning into the bilayer. PEG was chosen because it contains hydrophilic groups adding in the solubility of the hapten-carrier. The haptens are very hydrophobic and can and have caused the carriers to precipitate making them unusable.

Another example of a spacer comprises the following 15-amino acid sequence expressed in three-letter notation, as commonly used in the art (Hausman, R E; Cooper, G M (2004). The Cell: a molecular approach. Washington D.C.: ASM Press. p. 51):

```
                                            (SEQ ID NO: 2)
    Gln Tyr Ile Lys Ala Arg Ser Lys Phe Ile

Gly Ile Thr Glu Leu
```

The peptide was derived from the universal T-helper epitope from tetanus toxoid, Gln Tyr Ile Lys Ala Asp Ser Lys Phe Ile Gly Ile Thr Glu Leu (SEQ ID NO:3) wherein arginine in position 6 is replaced with asparagine. However, any sequence will have a similar effect as long as it retains the hapten at sufficient distance away from the membrane and it is sufficiently hydrophilic such that it does not partition into the lipid bilayer pulling the hapten very close to the membrane. There are other T-cell helper epitopes described in the scientific literature. A T-cell helper epitope could be specifically selected for a given species, such as humans, but the vaccine would only be expected to work in humans, making it the vaccine poorly functional in animals.

The amount of hapten that is conjugated carrier and/or per liposome regulates the immune response induced by the hapten. Various strategies which are known in the art can be used in accordance with the invention to optimize the amount of conjugated hapten. For example, the extent of derivatization of the protein with cross-linker can be influenced by varying experimental conditions such as the concentration of each of the reaction partners, the excess of one reagent over the other, the pH, the temperature, and the ionic strength. Similarly, the degree of coupling, i.e., the amount of hapten per liposome, can be adjusted by varying the experimental conditions described above to match the requirements of the vaccine. The ratio of liposome to hapten utilized to prepare the inventive synthetic liposomes of the present invention can be, for example, 1:1 or more, e.g., 1:3 or more, 1:10 or more, or 1:30 or more. Alternatively, or in addition, the ratio can be 1:1000 or less, e.g., 1:500 or less, 1:300 or less, or 1:100 or less. Thus, the ratio can be bounded by any two of the above endpoints. For example, the ratio can be 1:-1:1000, 1:3-1:500, 1:10-1:300, 1:10-:100, or 1:30-:100.

In one aspect, the immunoconjugate comprising for example a Hapten-crosslinker-spacer-peptide-spacer-MPER is produced and purified, and then placed with the liposome. Liposomes range in size from 75 nm to several microns. Placement could include allowing the liposome to form in the presence of the immunoconjugate to produce a partially embedded immunoconjugate. Alternatively, the immunoconjugate can be associated or attached to the liposome. Varying copies of the immunoconjugate complex can be inserted or associated/attached to the liposome. Also, multiple haptens can be added to an immunoconjugate by chemically making a branch on the PEG spacer, for example. The ratio of hapten to carrier is dependent upon number of lysines and amount of hapten added to the reaction. There generally are less than 100 lysines in proteins.

When the immunoconjugate is not attached or associated with the liposome, as for the tetanus-hapten immunoconjugate described in the Examples, the hapten is coupled to the free amines (lysines) on the surface of the tetanus toxoid. Methods for coupling the haptens to other protein carriers, adding spacers or linkers are known in the art and described previously. In the Examples below, a spacer was inserted between the TT and the hapten. Since PEG adds hydrophilic molecules, $PEG_2$ was used to keep the TT from precipitating when the hydrophobic haptens are added.

Once the carrier proteins have been conjugated to haptens, the relative extent of conjugation can be determined qualitatively by Western blotting for the hapten and quantitatively by mass spectrometry (e.g., MALD-TOF MS) or by measuring free functional groups on the protein by colorimetric assay.

Assuming equal affinity for hapten, there may be a direct correlation between antibody titer and vaccine efficacy. Therefore, increasing the amount of hapten that is conjugated to the protein may enhance the immunogenicity thereof.

In one aspect, the hapten is from an abuse-relevant drug or peptide. As used herein, the phrase "abuse-relevant" drug refers to any biologically effective substance or composition, which is subject to regulatory restrictions. Abuse-relevant drugs also refer to substances or compositions, which are contained in pharmaceuticals and which are prone to attempts of being extracted or separated from the pharmaceutical composition. Said extracted or enriched substance might later be abused for purposes not intended by the original pharmaceutical. For example, opiates comprised in pharmaceuticals for synergistic effects together with pain-killing substances, might be extracted to satisfy the needs of opiate addicts. "Abuse-deterrent" drug formulations are characterized by features which render a separation or extraction of the abuse-relevant drug from its pharmaceutical formulation, e.g. by mechanical, physical or chemical means, more difficult or impossible. Haptenic moieties can be derived from drugs commonly used in substance abuse, as defined in "Diagnostic and Statistical Manual of Mental Disorders", 4th Edition, Amer. Psychiatric Pub. June 2000.

The hapten can be natural or synthetic, from any desired antigen or drug, an analog of the antigen, enzyme or drug, a metabolic product of a drug, enzyme, or substrate, or a by-product of a drug or toxin, or from a compound which has structural or stereochemical features of any of these such that antibodies to the hapten will cross react with the antigen, toxin or drug itself.

In one embodiment, since heroin degrades to morphine, several of the heroin haptens can be used in an immunoconjugate for morphine, such as haptens 1, 2, 3, 4, 6 in FIG. 1, for example. For a review of morphine haptens please see Shen et al., 2012, Clinical Pharmacology & Therapeutics 91, 60.

In another embodiments, the hapten can be for methamphetamine or an analog thereof. Examples of such haptens are described in U.S. Pat. No. 8,299,222 to Owens et al., U.S. Pat. No. 7,217,802 to McConnell et al., among others.

In another embodiment, the hapten can be nicotine. Several nicotine haptens, carriers, and methods of conjugation have been described. The hapten can also be an analog of nicotine. Suitable nicotine analogs include any nicotine analog that induces an immune response in a mammal (humoral or cell-mediated). Nicotine analogs are known in the art (see, e.g., Cerny et al., Onkologie, 25: 406-411 (2002); Lindblom et al., Respiration, 69: 254-260 (2002); de Villiers et al., Respiration, 69: 247-253 (2002); Tuncok et al., Exp. Clin. Psychopharmacol., 9: 228-234 (2001); Hieda et al., Int. J. Immunopharmacol., 22: 809-819 (2000); Pentel et al., Pharmacol. Biochem. Behay., 65: 191-198 (2000); Isomura et al., J. Org. Chem., 66: 4115-4121 (2001); and Meijler et al., J. Am. Chem. Soc., 125: 7164-7165 (2003). For example, the nicotine analog can be N-succinyl-6-amino-(+/−)-nicotine (Castro et al., Biochem. Biophys. Res. Commun., 67: 583-589 (1975)), 6-(sigma-aminocapramido)-(+/−)-nicotine (Noguchi et al., Biochem. Biophys. Res. Comm., 83: 83-86 (1978)), O-succinyl-3'-hydroxymethyl-nicotine (Langone et al., Biochemistry, 12: 5025-5030 (1973); and Meth. Enzymol., 84: 628-640 (1982)), or 3'-(hydroxymethyl)-nicotine hemisuccinate (Langone et al., supra, Abad et al., Anal. Chem., 65: 3227-3231 (1993)). Additional examples of nicotine analogs suitable for use in the invention are described in U.S. Pat. Nos. 6,232,082 and 6,932,971. In a preferred embodiment, the nicotine analog is AM3. Novel nicotine analogs, both natural and derived, also can be used in the context of the invention, and examples of novel nicotine analogs are described in, e.g., International Patent Application Publication WO 2009/149252.

In another embodiment, the hapten can be cocaine. For example, the free acid of cocaine, diazonium salts of benzoyl cocaine and benzoyl ecognine, or the para-imino ester derivatives of cocaine and norcocaine (described in, e.g., U.S. Pat. Nos. 4,123,431; 4,197,237; and 6,932,971) can be conjugated to a liposome. A cocaine analog preferably is designed such that chemical coupling to the liposome minimizes the formation of non-cocaine like structures, yet maintains the antigenic determinant of the cocaine moiety (see, e.g., Carrera et al., Nature, 378: 727-730 (1995)). Additional examples of cocaine analogs suitable for use as a hapten of the invention are described in U.S. Pat. No. 5,876,727. In addition, the hapten can be an acylated ecgonine methyl ester, a succinylated ecgonine methyl ester, a succinylated norcocaine, or benzoyl ecgonine. Preferably, the antigen is the cocaine analog 6-(2R,3S)-3-(benzoyloxy)-8-methyl-8-azabicyclo[3.2.1] octane-2-carbonyloxy-hexanoic acid (GNC) or 6-((2R,3S)-3-(benzoyloxy)-8-methyl-8-azabicyclo[3.2.1]octane-2-carboxamido)hexanoic acid) (GNE).

Haptens from other drugs are known in the art or can be made by methods known in the art and exemplified herein. Examples of abuse-relevant drugs include: Analgesics, such as, for example; Opioids, Natural opium alkaloids, semisynthetic opium alkaloids, Morphine, Opium, Hydromorphone, Nicomorphine, Oxycodone, Dihydrocodeine, Diamorphine, Papaveretum, Codeine, Phenylpiperidine derivatives, Ketobemidone, Pethidine, Fentanyl, Diphenylpropylamine derivatives, Dextromoramide, Piritramide, Dextropropoxyphene, Bezitramide, Methadone, Benzomorphan derivatives, Pentazocine, Phenazocine, Oripavine derivatives, Buprenorphine, Morphinan derivatives, Butorphanol, Nalbuphine, Tilidine, Tramadol, Dezocine, Salicylic acid and derivatives, Acetylsalicylic acid, Aloxiprin, Choline salicylate, Sodium salicylate, Salicylamide, Salsalate, Ethenzamide, Morpholine salicylate, Dipyrocetyl, Benorilate, Diflunisal, Potassium salicylate, Guacetisal, Carbasalate calcium, Imidazole salicylate, Pyrazolones, Phenazone, Metamizole sodium, Aminophenazone, Propyphenazone, Nifenazone, Anilides, Paracetamol, Phenacetin, Bucetin, Propacetamol, Other analgesics and antipyretics, Rimazolium, Glafenine, Floctafenine, Viminol, Nefopam, Flupirtine, Ziconotide, Allylprodine, Prodine, Alphaprodine, Betaprodine, Anileridine, Benzylmorphine, Bezitramide, Buprenorphine, Clonitazene, Diampromide, Dihydromorphine, Dimenoxadol, Dimepheptanol, Dimethylthiambutene, Dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levophenacylmorphan, levorphanol, lofentanil, meperidine, meptazinol, metazocine, methadone, metopon, morphine, myrophine, nalbulphine, narceine, nicomorphine, norpipanone, opium, oxycodone, oxymorphone, papvretum, paladone, pentazocine, phenadoxone, phenazocine, phenomorphan, phenoperidine, piminodine, propiram, propoxyphene, sufentanil, tapenadol, tilidine, and tramadol; Anesthetics, such as, for example; Ethers, Diethyl ether, Vinyl ether, Halogenated hydrocarbons, Halothane, Chloroform, Methoxyflurane, Enflurane, Trichloroethylene, Isoflurane, Desflurane, Sevoflurane, Barbiturates, Methohexital, Hexobarbital, Thiopental, Narcobarbital, Opioid anesthetics, Fentanyl, Alfentanil, Sufentanil, Phenoperidine, Anileridine, Remifentanil, Other general anesthetics, Droperidol, Ketamine, Propanidid, Alfaxalone, Etomidate, Propofol, Hydroxybutyric acid, Nitrous oxide, Esketamine, Xenon, Esters of aminobenzoic acid, Metabutethamine, Procaine, Tetracaine, Chloroprocaine, Benzocaine, Amides, Bupivacaine, Lidocaine, Mepivacaine, Prilocaine, Butanilicaine, Cinchocaine, Etidocaine, Articaine, Ropivacaine, Levobupivacaine, Esters of benzoic acid, Cocaine, Other local anesthetics, Ethyl chloride, Dyclonine, Phenol, Capsaicin; Antiepileptic drug substances such as, for example; Barbiturates and derivatives, Methylphenobarbital, Phenobarbital, Primidone, Barbexaclone, Metharbital, Hydantoin derivatives, Ethotoin, Phenytoin, Amino(diphenylhydantoin) valeric acid, Mephenytoin, Fosphenytoin, Oxazolidine derivatives, Paramethadione, Trimethadione, Ethadione, Succinimide derivatives, Ethosuximide, Phensuximide, Mesuximide, Benzodiazepine derivatives, Clonazepam, Carboxamide derivatives, Carbamazepine, Oxcarbazepine, Rufinamide, Fatty acid derivatives, Valproic acid, Valpromide, Aminobutyric acid, Vigabatrin, Progabide, Tiagabine, Other antiepileptics, Sultiame, Phenacemide, Lamotrigine, Felbamate, Topiramate, Gabapentin, Pheneturide, Levetiracetam, Zonisamide, Pregabalin, Stiripentol, Lacosamide, Beclamide; Antipsychotic drug substances, such as, for example; Phenothiazines with an aliphatic side-chain, Chlorpromazine, Levomepromazine, Promazine, Acepromazine, Triflupromazine, Cyamemazine, Chlorproethazine, Phenothiazines with piperazine structure, Dixyrazine, Fluphenazine, Perphenazine, Prochlorperazine, Thiopropazate, Trifluoperazine, Acetophenazine, Thioproperazine, Butaperazine, Perazine, Phenothiazines with piperidine structure, Periciazine, Thioridazine, Mesoridazine, Pipotiazine, Butyrophenone derivatives, Haloperidol, Trifluperidol, Melperone, Moperone, Pipamperone, Bromperidol, Benperidol, Droperidol, Fluanisone, Indole derivatives, Oxypertine, Molindone, Sertindole, Ziprasidone, Thioxanthene derivatives, Flupentixol, Clopenthixol, Chlorprothixene, Tiotixene, Zuclopenthixol, Diphenylbutylpiperidine derivatives, Fluspirilene, Pimozide, Penfluridol, Diazepines, oxazepines and thiazepines, Loxapine, Clozapine, Olanzapine, Quetiapine, Neuroleptics, in tardive dyskinesia, Tetrabenazine, Benzamides, Sulpiride, Sultopride, Tiapride, Remoxipride, Amisulpride, Veralipride, Levosulpiride, Lithium, Other antipsychotics, Prothipendyl, Risperidone, Clotiapine, Mosapramine, Zotepine, Aripiprazole, Paliperidone; Hypnotic and sedative drug substances, such as, for example; Barbiturates, Pentobarbital, Amobarbital, Butobarbital, Barbital, Aprobarbital, Secobarbital, Talbutal, Vinylbital, Vinbarbital, Cyclobarbital, Heptabarbital, Reposal, Methohexital, Hexobarbital, Thiopental, Etallobarbital, Allobarbital, Proxibarbal, Aldehydes and derivatives, Chloral hydrate, Chloralodol, Acetylglycinamide chloral hydrate, Dichloralphenazone, Paraldehyde, Benzodiazepineemepronium derivatives, Flurazepam, Nitrazepam, Flunitrazepam, Estazolam, Triazolam, Lormetazepam, Temazepam, Midazolam, Brotizolam, Quazepam, Loprazolam, Doxefazepam, Cinolazepam, Piperidinedione derivatives, Glutethimide, Methyprylon, Pyrithyldione, Benzodiazepine related drugs, Zopiclone, Zolpidem, Zaleplon, Ramelteon, Other hypnotics and sedatives, Methaqualone, Clomethiazole, Bromisoval, Carbromal, Scopolamine, Propiomazine, Triclofos, Ethchlorvynol, Valerian, Hexapropymate, Bromides, Apronal, Valnoctamide, Methylpentynol, Niaprazine, Melatonin, Dexmedetomidine, Dipiperonylaminoethanol; Anxiolytic drug substances, such as, for example; Benzodiazepine derivatives, Diazepam, Chlordiazepoxide, Medazepam, Oxazepam, Potassium clorazepate, Lorazepam, Adinazolam, Bromazepam, Clobazam, Ketazolam, Prazepam, Alprazolam, Halazepam, Pinazepam, Camazepam, Nordazepam, Fludiazepam, Ethyl loflazepate, Etizolam, Clotiazepam, Cloxazolam, Tofisopam, Diphenylmethane derivatives, Hydroxyzine, Captodiame, Carbamates, Meprobamate, Emylcamate, Mebutamate, Dibenzo-bicyclo-octadiene derivatives, Benzoctamine, Azaspirodecanedione derivatives, Buspirone, Other anxiolytics, Mephenoxalone, Gedocamil, Etifoxine. Antidepressant drug substances, such as, for example tricyclic antidepressants, non-selective monoamine reuptake inhibitors, Desipramine, Imipramine, Imipramine oxide, Clomipramine, Opipramol, Trimipramine, Lofepramine, Dibenzepin, Amitriptyline, Nortriptyline, Protriptyline, Doxepin, Iprindole, Melitracen, Butriptyline, Dosulepin, Amoxapine, Dimetacrine, Amineptine, Maprotiline, Quinupramine, Selective serotonin reuptake inhibitors, Zimeldine, Fluoxetine, Citalopram, Paroxetine, Sertraline, Alaproclate, Fluvoxamine, Etoperidone, Escitalopram, Monoamine oxidase inhibitors, non-selective, Isocarboxazid, Nialamide, Phenelzine, Tranylcypromine, Iproniazide, Iproclozide, Monoamine oxidase A inhibitors, Moclobemide, Toloxatone, Other antidepressants, Oxitriptan, Tryptophan, Mianserin, Nomifensine, Trazodone, Nefazodone, Minaprine, Bifemelane, Viloxazine, Oxaflozane, Mirtazapine, Medifoxamine, Tianeptine, Pivagabine, Venlafaxine, Milnacipran, Reboxetine, Gepirone, Duloxetine, Agomelatine, Desvenlafaxine, Centrally acting sympathomimetics, Amphetamine, Dexamphetamine, Metamphetamine, Methylphenidate, Pemoline, Fencamfamin, Modafinil, Fenozolone, Atomoxetine, Fenetylline, Xanthine derivatives, Caffeine, Propentofylline, Other psychostimulants and nootropics, Meclofenoxate, Pyritinol, Piracetam, Deanol, Fipexide, Citicoline, Oxiracetam, Pirisudanol, Linopirdine, Nizofenone, Aniracetam, Acetylcarnitine, Idebenone, Prolintane, Pipradrol, Pramiracetam, Adrafinil, Vinpocetine; Drug substances used in addictive disorders, such as, for example; Nicotine, Bupropion, Varenicline, Disulfiram, Calcium carbimide, Acamprosate, Naltrexone, Buprenorphine, Methadone, Levacetylmethadol, Lofexidine. Antivertigo drug substances, such as, for example; Betahistine, Cinnarizine, Flunarizine, Acetylleucine, other nervous system drugs, Gangliosides and ganglioside derivatives, Tirilazad, Riluzole, Xaliproden, Hydroxybutyric acid, Amifampridine; Further abuse-relevant drugs are Ethylmorphine, Codeine, Opium alkaloids with morphine, Normethadone, Noscapine, Pholcodine, Dextromethorphan, Thebacon, Dimemorfan, Acetyldihydrocodeine, Benzonatate, Benproperine, Clobutinol, Isoaminile, Pentoxyverine, Oxolamine, Oxeladin, Clofedanol, Pipazetate, Bibenzonium bromide, Butamirate, Fedrilate, Zipeprol, Dibunate, Droxypropine, Prenoxdiazine, Dropropizine, Cloperastine, Meprotixol, Piperidione, Tipepidine, Morclofone, Nepinalone, Levodropropizine, Dimethoxanate; Further abuse-relevant drugs are opioid agonists/antagonists such as Cyclazonine opiate analogues such as Desomorphine.

Haptens for compounds other than drugs, such as, for example, small molecule toxins and poisons, can also be used to make the liposome-hapten composition of the present invention. In addition, haptens from antigens of disease-causing organisms, or from enzymes or metabolites implicated in certain conditions, such as obesity, diabetes, Alzheimer's, hairloss, or dental caries, to name a few, wherein an immune response would alleviate the condition are also envisioned.

The liposome-hapten composition of the invention is suitably included in an immunogenically effective amount in a composition with a physiologically acceptable vehicle. A "physiologically acceptable" vehicle is any vehicle that is suitable for in vivo administration (e.g., oral, transdermal or parenteral administration) or in vitro use, i.e., cell culture. An "immunogenically effective amount," as used herein, is an amount of liposome-hapten composition which is capable of inducing an immune response in an animal which significantly engages agents that share immunological features with the hapten. The actual amount of the hapten may vary depending on the animal to be immunized, the route of administration and adjuvants. Immunogenic dosages can be determined by those of skill in the art. The immune response may be indicated by T and/or B cell responses. Typically, the immune response is detected by the presence of antibodies that specifically bind to a particular polypeptide. Methods of detecting antibodies are known to those of skill in the art and include such assays as ELISA assays, ELISPOT assays, western blot assays, and competition assays.

The liposome-hapten conjugates of the invention may be mixed with excipients which are pharmaceutically acceptable and compatible with the active ingredient. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, and combinations thereof. The immunogenic compositions of the invention can additionally include: pH buffering agents; lubricating agents such as talc, magnesium stearate, and mineral oil; wetting agents; emulsifying and suspending agents; and preserving agents such as methyl- and propylhydroxy-benzoates.

In another embodiment, a liposome-hapten conjugate composition is administered to a mammal (e.g., a human), whereupon an immune response against the hapten, or the antigen from which the hapten is derived, is induced. The immune response can be a humoral immune response, a cell-mediated immune response, or, desirably, a combination of humoral and cell-mediated immunity. Ideally, the immune response provides a clinical benefit upon exposure to the antigen. When the antigen is an addictive drug, or analog thereof, a "clinical benefit" can be, for example, a reduction in the physiological effects of the addictive drug, a reduction in the reward or pleasure associated with use of the addictive drug, or a reduction in the likelihood of regaining an addiction to the drug. However, a clinical benefit is not required in the context of the invention. The inventive method further can be used for antibody production and harvesting. For example, the inventive method can be used to produce antibodies for diagnostic purposes (e.g., to detect the presence of an addictive drug or an antigen in the blood).

Administering the liposome-hapten conjugate can be one component of a multistep regimen for inducing an immune response in a mammal. In particular, the inventive method can represent one aim of a prime and boost immunization regimen. In this respect, the method further comprises administering to the mammal a boosting composition after administering the composition comprising the inventive liposome-hapten conjugate to the mammal. In this embodiment, therefore, the immune response is "primed" upon administration of the composition containing the inventive conjugate, and is "boosted" upon administration of the boosting composition. Alternatively, the inventive method further comprises administering to the mammal a priming composition to the mammal prior to administering the composition comprising the inventive conjugate to the mammal. In this embodiment, therefore, the immune response is "primed" upon administration of the priming composition, and is "boosted" upon administration of the composition containing the adenovirus-antigen conjugate.

Administration of the priming composition and the boosting composition can be separated by any suitable timeframe, e.g., 1 week or more, 2 weeks or more, 4 weeks or more, 8 weeks or more, 12 weeks or more, 16 weeks or more, 24 weeks or more, 52 weeks or more, or a range defined by any two of the foregoing values. The boosting composition preferably is administered to a mammal (e.g., a human) 2 weeks or more (e.g., 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 20 weeks, 24 weeks, 28 weeks, 35 weeks, 40 weeks, 50 weeks, 52 weeks, or a range defined by any two of the foregoing values) following administration of the priming composition. More than one dose of priming composition and/or boosting composition can be provided in any suitable timeframe. The dose of the priming composition and boosting composition administered to the mammal depends on a number of factors, including the extent of any side-effects, the particular route of administration, and the like.

Any route of administration can be used to deliver the conjugate to the mammal. Indeed, although more than one route can be used to administer the conjugate, a particular route can provide a more immediate and more effective reaction than another route. Preferably, the conjugate is administered via intramuscular injection. A dose of conjugate also can be applied or instilled into body cavities, absorbed through the skin (e.g., via a transdermal patch), inhaled, ingested, topically applied to tissue, or administered parenterally via, for instance, intravenous, peritoneal, or intraarterial administration.

The conjugate can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the conjugate. The conjugate also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The dose of liposome-hapten conjugate administered to the mammal will depend on a number of factors, including the size of a target tissue, the extent of any side-effects, the particular route of administration, and the like. The dose ideally comprises an "effective amount" of conjugate, i.e., a dose of conjugate which provokes a desired immune response in the mammal or production of the desired quantity of antibodies in the mammal. The desired immune response can entail production of antibodies, protection upon subsequent challenge, immune tolerance, immune cell activation, and the like. Similarly, the desired quantity of antibodies can provide protection upon subsequent challenge, immune tolerance, and the like.

The liposome-hapten conjugate can be administered in conjunction with counseling and/or one or more additional agents that prevent or treat drug addiction. The additional agent may treat withdrawal symptoms, facilitate quitting, or prevent relapse. When the liposome is conjugated to a nicotine hapten, the additional agent can be, for example, an anti-depressant, a nicotine receptor modulator, a cannabinoid receptor antagonist, an opioid receptor antagonist, a monoamine oxidase inhibitor, an anxiolytic, or any combination of these agents. Preferably, the additional agent is an anti-depressant selected from the group consisting of bupropion, doxepin, desipramine, clomipramine, imipramine, nortriptyline, amitriptyline, protriptyline, trimipramine, fluoxetine, fluvoxamine, paroxetine, sertraline, phenelzine, tranylcypromine, amoxapine, maprotiline, trazodone, venlafaxine, mirtazapine, and pharmaceutically active salts or optical isomers thereof. When the adenovirus is conjugated to a cocaine hapten, the additional agent can be, for example, an opioid receptor antagonist, an anti-depressant such as desipramine or fluoxetine, or an agent which regulates the dopaminergic system (e.g., bromocriptine or buprenorphine).

It is anticipated that dosages of liposome-hapten conjugate in the range from about 0.1 ug/kg body weight to about 10 mg/kg body weight are contemplated, such as in the range from about 500 ug/kg body weight to about 1000 ug/kg body weight, will prevent or reduce symptoms at least 50% compared to pre-treatment symptoms. It is specifically contemplated that vaccine preparations and compositions of the invention may palliate or alleviate the undesirable condition without providing a cure, or, in some embodiments, may be used to inhibit or prevent onset of the condition.

Antibodies Specific for Haptens

The present invention also provides antibodies that immunoreact with the haptens of this invention. The antibodies may be of any of the immunoglobulin subtypes IgA, IgD, IgG, IgE, or IgM. Antibodies may be produced by any means known in the art and may be, e.g., monoclonal antibodies, polyclonal antibodies, phage display antibodies, and/or human recombinant antibodies. A recombinant antibody can be manipulated or mutated so as to improve its affinity or avidity for the antigen. Means of such manipulation are well known in the art.

In some embodiments, human antibodies or humanized antibodies may be used in passive immunization protocols. Methods to humanize murine monoclonal antibodies via several techniques may be used and are well known in the art. Further, methodologies for selecting antibodies with desired specificity from combinatorial libraries make human monoclonal antibodies directly available. If desired, protein engineering may be utilized to prepare human IgG constructs for clinical applications such as passive immunization of a subject. In passive immunization, a short-term immunization is achieved by the transfer of antibodies to a subject. The antibodies can be administered in a physiologically acceptable vehicle which can be administered by any suitable route, e.g., intravenous (IV) or intramuscular (IM). Any antibodies of the invention described herein may be suitably used, such as monoclonal antibodies (mAb).

The passive administration of antibodies should prove beneficial to reduce serum levels of the drug or antigen source of the hapten and attenuate the antigen's, drug's, or its metabolic product's (cardiovascular, metabolic, endocrine) effects. It can also be used in weekly or biweekly pharmacotherapy during drug cessation programs. The pharmacotherapy could entail self-injection of mAb to maintain a high circulating level of antibody.

In some embodiments, active immunization (liposome-hapten conjugate vaccine) and passive immunization (antibodies) may be used in combination in a subject. The effective dose of either the liposome-hapten conjugate vaccine or antibodies may be the effective dose of either when administered alone. In some embodiments, the effective dose of either in combination with the other may be less than the amount that would be therapeutically effective if either is administered alone.

Some embodiments of the invention provide a method of reducing drug withdrawal symptoms in a subject. Reducing withdrawal symptoms of a drug can encompass, but is not limited to, reducing craving for the drug, irritability, anxiety, restlessness, depressed mood, drowsiness, difficulty concentrating, insomnia, somatic complaints, increased appetite, or weight gain in the subject. Methods of reducing withdrawal symptoms may be accomplished by administering to the subject the liposome formulations described above in combination with passive immunization or other adjunct therapies used in drug cessation.

It will be appreciated that the specific dosage of liposome-hapten conjugate or antibodies administered in any given case will be adjusted in accordance with the condition of the subject and other relevant medical factors that may modify the activity of the liposome-hapten conjugate or antibody or the response of the subject, as is well known by those skilled in the art. For example, the specific dose for a particular patient depends on age, body weight, general state of health, diet, the timing and mode of administration, the rate of excretion and medicaments used in combination. Dosages for a given patient can be determined using conventional considerations such as by means of an appropriate conventional pharmacological protocol.

Reagents for preparing a liposome-hapten composition of the present invention can be provided in the form of kits. Such a kit can contain L(MPLA), L(MPLA) with a carrier embedded in the liposome and/or one or more carriers, and a system for (means enabling) conjugation of a desired hapten to the liposome. In one embodiment, a kit contains a mixture of suitable linkers, spacers, reagents or means for preparing such mixtures, and/or reagents for detecting liposome-hapten conjugates. Other components of a kit can easily be determined by one of skill in the art. In one embodiment, the liposome composition is lyophilized.

It is specifically contemplated that any embodiment of any method or composition of the invention may be used with any other method or composition of the invention. As used in this specification and the appended claims, the singular forms "a," "an," and "the" include plural referents unless the content clearly dictates otherwise. Thus, for example, reference to a composition containing "an antibody" includes a mixture of two or more antibodies. It should also be noted that the term "or" is generally employed in its sense including "and/or" unless the content clearly dictates otherwise. It also is specifically understood that any numerical value recited herein includes all values from the lower value to the upper value, i.e., all possible combinations of numerical values between the lowest value and the highest value enumerated are to be considered to be expressly stated in this application. For example, if a range is stated as 1% to 50%, it is intended that values such as 2% to 40%, 10% to 30%, or 1% to 3%, etc., are expressly enumerated in this specification.

The following examples are included to demonstrate preferred embodiments of the invention. It should be appreciated by those of skill in the art that the techniques disclosed in the examples which follow represent techniques discovered by the inventors and thought to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The following Materials and Methods were used in the Examples below.

Materials and Reagents 1,2-Dimyristoyl-sn-glycero-3-phosphoglycerol (DMPG); 1,2-dimyristoyl-sn-glycero-3-phosphate (DMPC), galactosyl ceramide (GalCer), monophosphoryl lipid A (PHAD™) (MPLA), and cholesterol (CHOL) were purchased from Avanti Polar Lipids (Alabaster, Ala.). Sulfo-3-GalCer (sulfatide), gelatin and bovine serum albumin (BSA) used as an ELISA blocker were purchased from Sigma-Aldrich (Saint Louis, Mo.). Tetanus toxoid (TT) was purchased from Statens Serum Institut (Copenhagen, Denmark). BSA used for coupling to haptens, SM(PEG)2 linker and BCA total protein assay kits were purchased from Pierce Protein Research/Thermo Fisher Scientific (Rockford, Ill.). Fmoc-dPEG4-OH was obtained from Quanta BioDesign (Powell, Ohio), while other Fmoc-protected amino acids and peptide synthesis reagents were purchased from Applied Biosystems (Foster City, Calif.). N,N'-maleoyl-γ-aminobutyryc acid and S-trityl-mercaptopropionic acid were obtained from Chem-Impex International (Wood Dale, Ill.). Immunolon 2HB flat and "U" bottom ELISA plates were purchased from Thermolab Systems. Peroxidase-linked sheep anti-mouse IgG (γ-chain specific) was purchased from The Binding Site. 2,2'-azino-di(3-ethylbenzthiazoline-6-sulfonate) peroxidase substrate system was purchased from KPL, Inc.

Haptens and Peptide Synthesis

Figure 2:
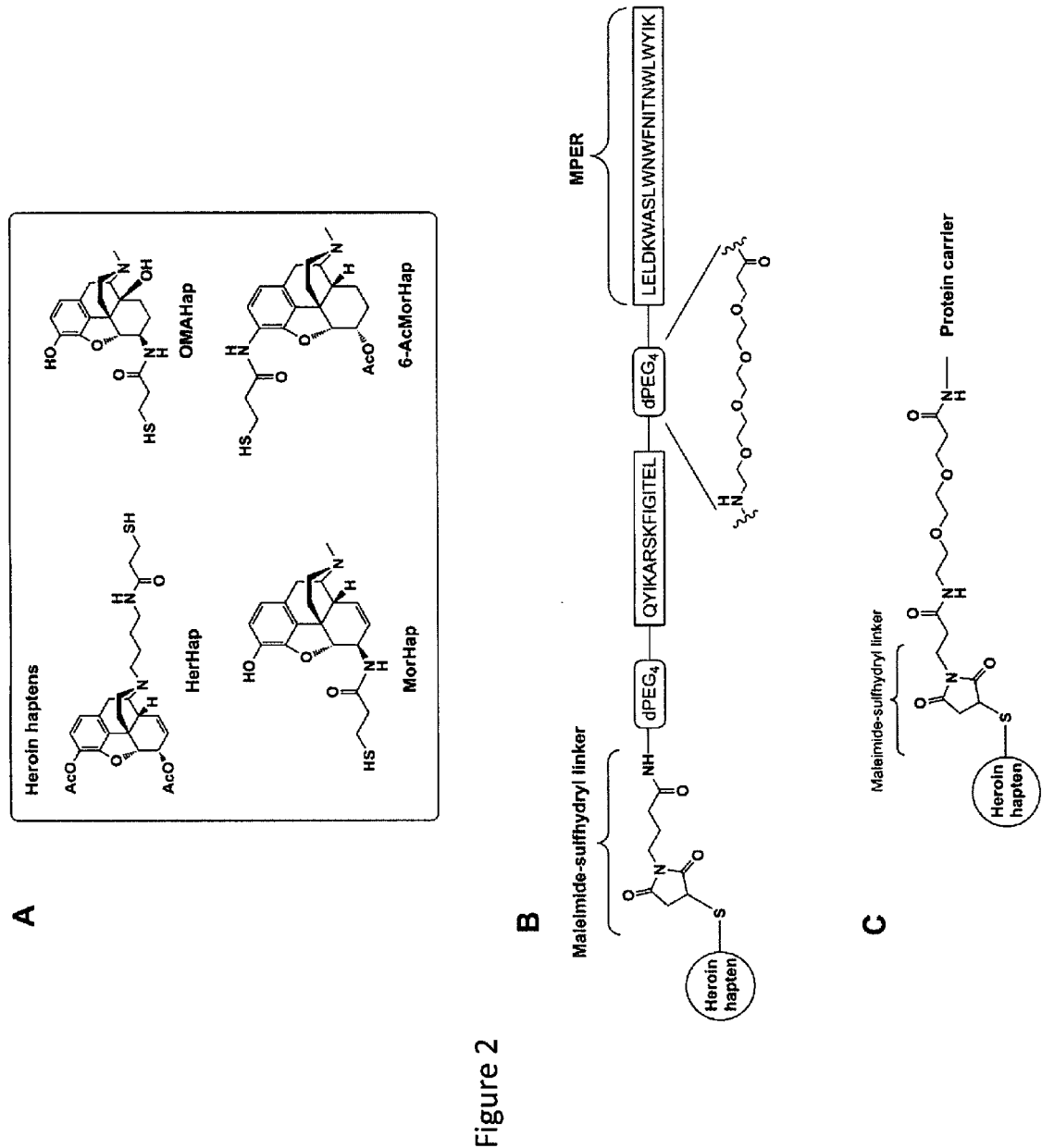
FIG. 2. Heroin haptens (A) and hapten coupling strategy to peptide (B) and protein (C) carriers used in the study. Haptens are coupled by maleimide-sulfhydryl linkages to linkers. The peptide coupling strategy attaches the peptide to a linker which is also attached to another peptide that is a universal T-cell epitope or a peptide spacer. The second peptide is attached to another spacer which is attached to a hapten.

The structures of the synthetic haptens and peptides used are shown in FIGS. 2A and 2B, respectively. HerHap was synthesized as previously described (Stowe et al., supra). OMAHap was synthesized from β-oxymorphamine, MorHap was synthesized from morphine, and 6-AcMorHap was synthesized from hydromorphone. The MPER carrier contains a 23 amino acid peptide derived from the membrane proximal external region (MPER) from the gp41 transmembrane HIV-1 envelope protein and a universal T cell epitope peptide. Peptides were synthesized using an Applied Biosystems 433A peptide synthesizer and a conventional Fmoc chemistry (Chan W C, White P D, eds. Fmos Solid Phase Peptide Synthesis: A Practical Approach. New York: Oxford University Press; 2000). The peptide sequences intended for conjugation with heroin/morphine haptens were capped with N,N'-maleoyl-γ-aminobutyryc acid using standard carbodiimide/HOBt coupling chemistry (Konig W, Geiger R, 1970, Chemische Berichte 103, 788-98), followed by cleavage with a mixture of 95% TFA, 2.5% water, and 2.5% triisopropylsilane (Sole N A, Barany G, 1992, J. Org. Chem. 57, 5399-5403). All peptides were purified by reverse-phase HPLC using a Shimadzu Prominence LC-6AD semi-preparative system, and characterized by mass-spectrometry using a Shimadzu LCMS-IT-TOF system (Shimadzu Scientific Instruments; Columbia, Md., USA).

Coupling of Haptens to Peptides and Protein Carriers

Conjugation of haptens with MPER carrier was performed by 1) removing the trityl protecting group from the haptens with 3% TFA, 3% triisopropylsilane in chloroform (30 min), followed by evaporation of volatile components under vacuum; 2) suspension of the residue in pH 7.4 PBS buffer at the concentration of about 10 mg/ml; 3) mixing the resulting suspension with a solution of MPER-carrier in 1:1 methanol-water at the concentration of about 2-5 mg/ml; 4) agitating the resulting mixture by sonication in a cleaning bath for 1-2 h. The progress of the conjugation was monitored by LC-MS using a Shimadzu LCMS-IT-TOF system equipped with a RP-UFLC column (Shim-Pack XR-ODS II, 2.0 mm×150 mm) (Shimadzu Scientific Instruments; Columbia, Md.). Purification of the conjugates was accomplished by HPLC on a Vydac 218TP152022 C18 column (Grace Davison Discovery Sciences; Deerfield, Ill.) using a Shimadzu Prominence LC-6AD semi-preparative HPLC system. The HPLC fractions containing the conjugates with the target masses, as determined by LC-MS, were pooled and lyophilized to yield hapten-MPER carrier conjugates in a powder form.

Conjugation of heroin/morphine haptens with TT and BSA carriers was performed by 1) activation of the protein carrier with SM(PEG)2 linker by mixing the protein and the linker solutions (1-2 mg of linker per 1 mg of protein) in pH 7.4 PBS at concentration of about 10 mg/ml and agitation by gentle shaking (1 h); 2) purification of the activated protein by dialysis in pH 7.4 PBS buffer; 3) removing the trityl protecting group from the haptens with 3% TFA, 3% triisopropylsilane in chloroform (30 min), followed by evaporation of volatile components under vacuum; 4) suspension of the residue in pH 7.4 PBS buffer at the concentration of about 10 mg/ml, followed by filtering off the insoluble particulate using Pall 0.2 µm Acrodisc syringe filters; 3) mixing the resulting filtrate with the activated protein solution, at about 1 mg of hapten per 1 mg of protein ratio; 4) agitating the resulting mixture by gentle shaking for 1 h; and 5) purification of the hapten-protein conjugate by dialysis in pH 6.5 PBS buffer. The resulting conjugate concentrations were measured by a microplate BCA total protein assay.

Preparation of Liposomes and Immunization

Liposomes were prepared as previously described (Matyas et al., 2003, Methods Enzymol. 373, 34-50). Four different liposome formulations were used for immunization with L(MPLA+HerHap-PEG-MPER carrier) and L(MPLA+OMAHap-PEG-MPER carrier). L(43% Chol) contained DMPC:CHOL:DMPG (molar ratio, 9:7.5:1). L(sulfo-GalCer) contained DMPC:CHOL:DMPG (9:7.5:1) with 5 mg/ml sulfo-GalCer. L(71% Chol) contained DMPC:CHOL:DMPG (9:25:1) (71% CHOL). L(GalCer) contained DMPC:CHOL:DMPG (9:7.5:1) with 2 mg/ml GalCer. The liposome formulations contained 200 µg/ml of MPLA and either 100 µg/ml of HerHap-PEG-MPER carrier, OMAHap-PEG-MPER carrier, MPER carrier, or MPER, which were dissolved in methanol and added to the chloroform:methanol lipid mixture prior to rotary evaporation. The final phospholipid concentration of the liposomes was 50 mM in PBS, pH 6.4. Liposomes containing MPLA that were mixed with for hapten-TT conjugates for immunization were L(43% Chol) containing the MPLA, but lacking peptide. The lyophilized liposomes were hydrated in PBS, pH 6.4, and mixed with hapten-TT conjugates to give a final dose of 10 µg TT/0.05 ml/mouse. Female BALB/c mice (5 mice/group; 6-8 weeks of age) (Charles River Laboratories, Indianapolis, Ind.) were immunized intramuscularly with 0.05 ml of liposomal vaccines.

ELISA

Hapten-BSA (0.1 µg BSA/0.1 ml/well in PBS, 6.4) was added to flat bottom plates and incubated at 4° C., overnight. The plates were blocked with 20 mM Tris-HCl-154 mM sodium chloride-1% BSA, pH 7.4 (blocker) (0.3 ml/well) at room temperature for 2 h. Serum (0.1 ml/well) diluted in blocker starting at 1:50 in serial 2-fold dilutions in triplicate was added to the plate. Following incubation at room temperature 1 h, the plates were washed 4 times with 0.5 ml/well of TBS-0.05% Tween 20®. Peroxidase-linked mouse anti-human IgG (0.1 µg in 0.1 ml blocker) was added and the plates incubated for 1 hr at room temperature. The plates were washed and 0.1 ml/well substrate was added. After incubation for 1 h at room temperature, the absorbance was read at 405 nm. The above procedure was used for measurement of antibodies to TT using TT (0.1 µg/well) as the coating antigen in PBS, pH 7.4. ELISA with peptides was conducted as described (Matyas et al., 2009, AIDS 23, 2069-2077). End point titer is defined as the dilution at which the absorbance is twice background as defined from wells lacking primary sera.

Example 1

Immune Response to Heroin Hapten-MPER Peptide Carrier Attached to Liposomes Containing MPLA Four liposome compositions were used as vehicles for immunization of 5 mice each with L(MPLA+HerHap-PEG-MPER carrier): liposomes containing 43% CHOL; liposomes containing 43% CHOL and sulfo-GalCer; liposomes containing 43% CHOL and GalCer; and liposomes containing 71% CHOL. Liposomes containing 43% CHOL have been routinely used in many clinical trials (Alving et al., 2012, Expert. Rev. Vaccines 11, 733-744), and 71% CHOL changes the biophysical structure to allow the induction of anti-CHOL antibodies (Swartz et al., 1988, PNAS USA 85, 1902-1906; Alving et al., 1991, Crit. Rev. Immunol. 10, 441-453). Sulfo-GalCer was examined as a lipid constituent because sulfo-GalCer was proposed as a potential anionic binding site for opiates (Loh et al., 1974, Life Sci 14, 2231-2245; Farooqui and Horrocks, 1985, Biochemistry 66, 87-95).

Figure 3:
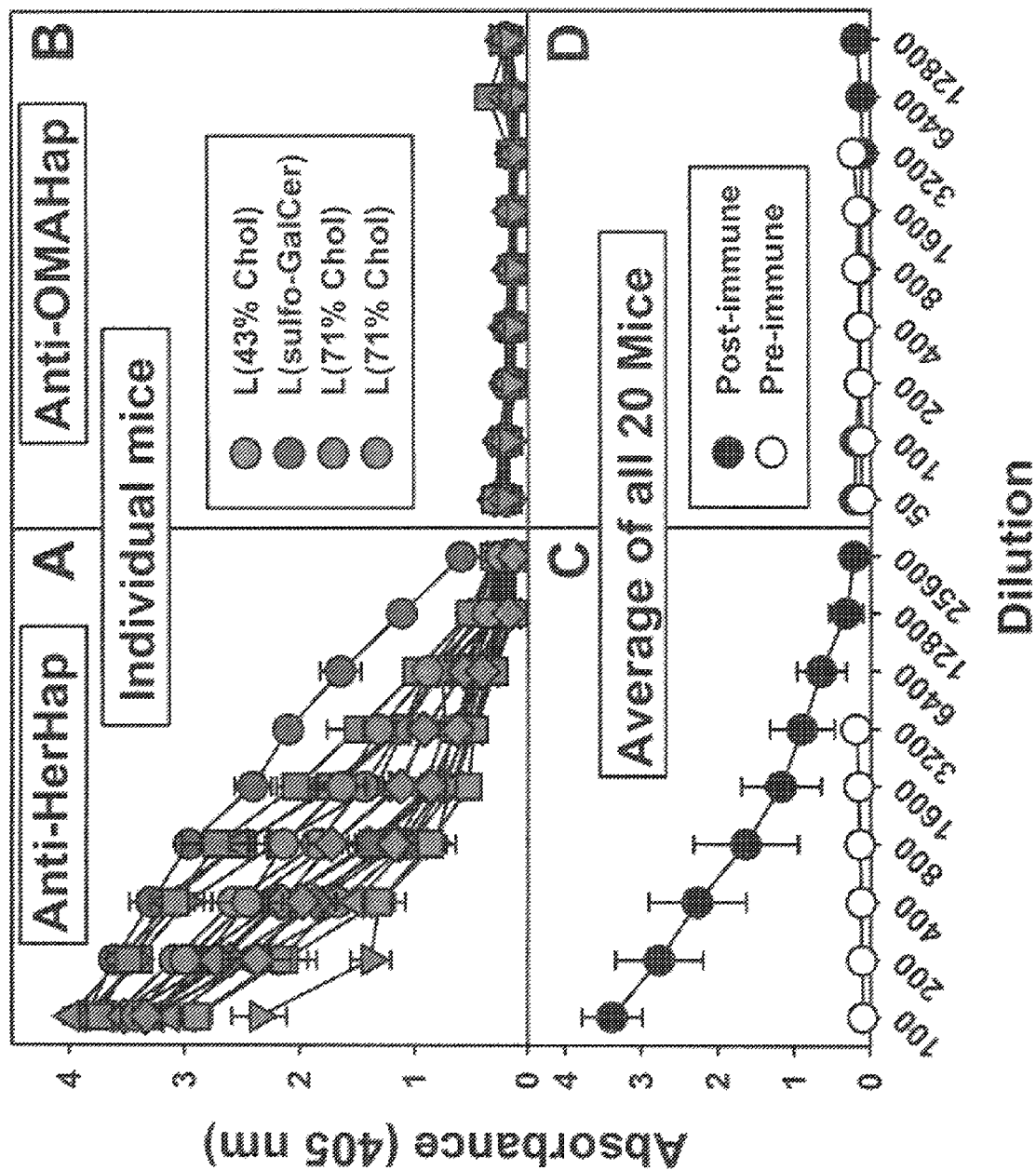
FIG. 3. Serum IgG responses to heroin haptens coupled to MPER carrier 9 weeks after primary immunization. Mice were immunized with L(MPLA+HerHap-PEG-MPER carrier) (A, C) or L(MPLA+OMAHap-PEG-MPER) (B, D) at week 0, 3 and 6. ELISA was conducted with the appropriate hapten coupled to BSA. Each curve represents an individual mouse (5 mice/liposome formulation). Each symbol (circle, triangle, square, diamond, inverted triangle) represents a different mouse in the group. Values represent the mean±standard deviation of triplicate determinations.

As shown in FIG. 3A, each of the 20 mice in the four different liposome groups mounted an immune response to the attached HerHap hapten, but no distinctive differences were observed between the liposome compositions. The average end point titer of antibodies to the hapten of all of the 20 mice taken together was approximately 12,800 (FIG. 3C). It is clear that the L(MPLA+HerHap-PEG-MPER carrier) was an excellent immunogen for induction of antibodies to a heroin hapten, and neither the induction nor the binding of antibodies was affected by sulfo-GalCer, GalCer, or 71% CHOL. In contrast to HerHap, no detectable antibodies to OMAHap were observed in 20 mice after immunization with L(MPLA+OMAHap-PEG-MPER) containing the same liposomal lipid combinations (FIG. 3B). Clearly OMAHap is a very poor hapten since it does not induce antibodies with or without a carrier.

Figure 4:
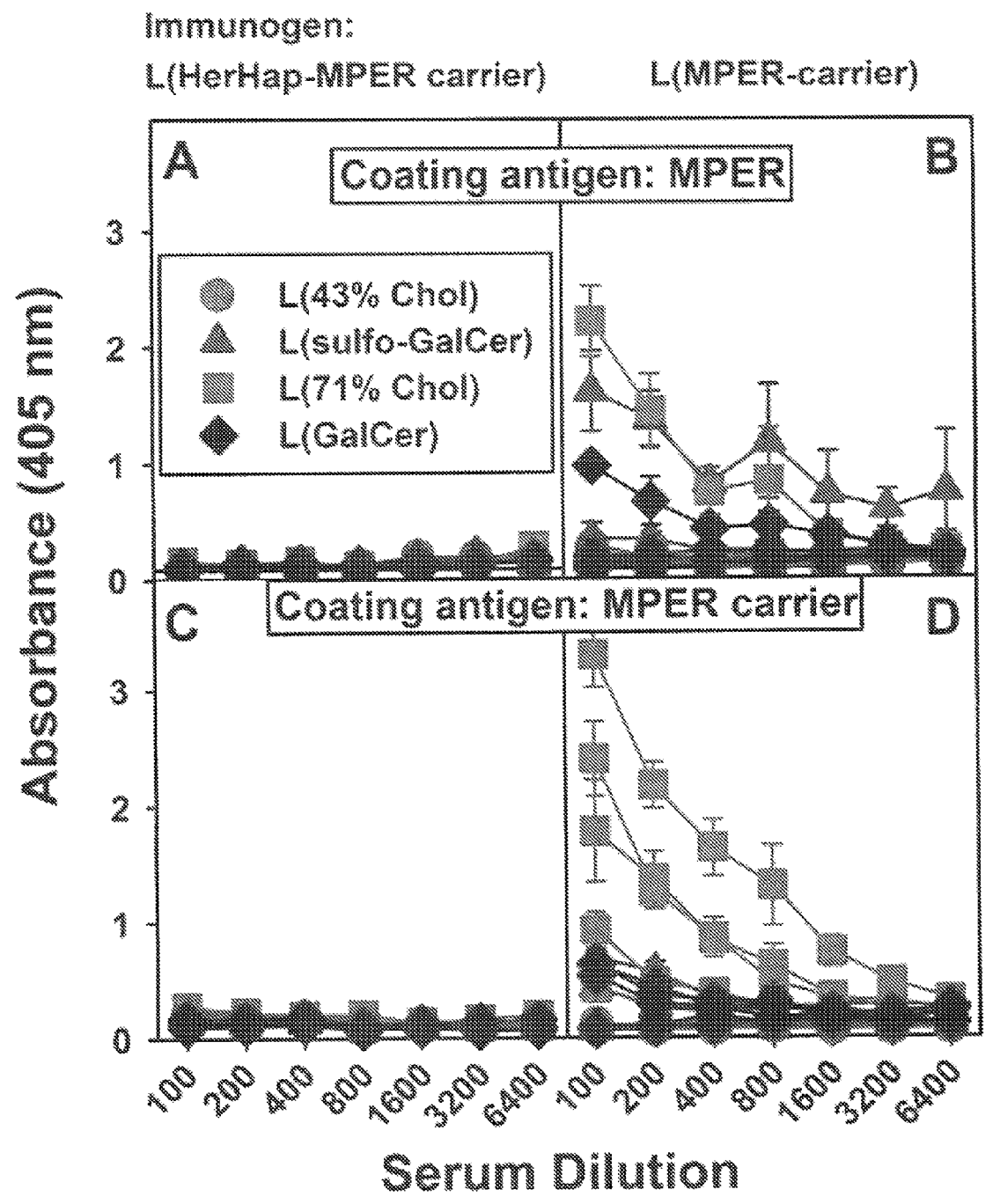

Despite the immune response to the hapten observed after immunization with L(MPLA+HerHap-PEG-MPER carrier), none of the 20 mice had any detectable antibodies either to MPER or MPER carrier (FIGS. 4A and 4C). Absence of antibodies to MPER was also observed after immunization with L(MPLA+OMAHap-PEG-MPER) (data not shown). Immune responses to MPER after immunization with L(MPLA+MPER) have been previously documented (Matyas et al., 2009, suprat) and antibodies to MPER and to MPER carrier were observed in many of the mice immunized with L(MPLA+MPER-carrier) (FIGS. 4B and 4D). Thus, the presence of either HerHap or OMAHap attached to the MPER carrier had a profound inhibitory effect on the ability of the mice to induce antibodies either to MPER itself or to the complete MPER carrier carrier.

Example 2

Figure 5:
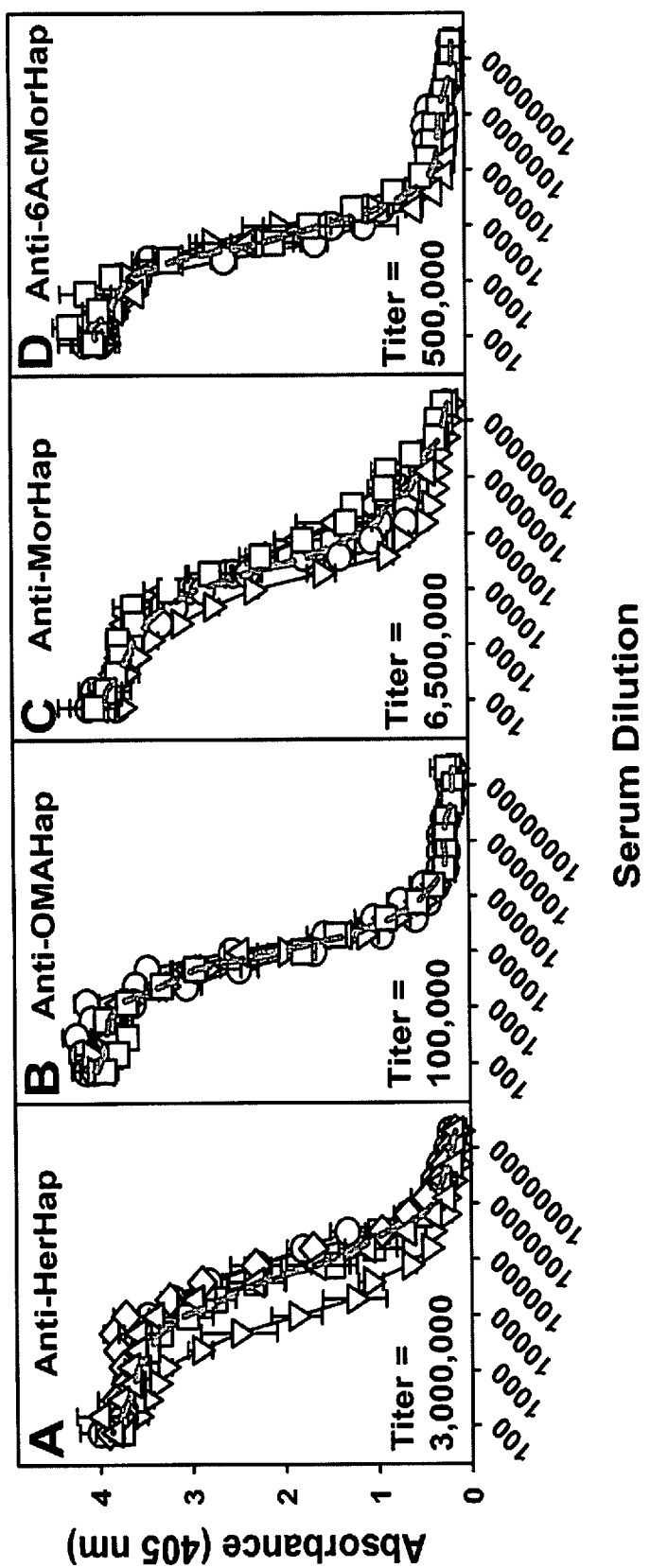
FIG. 5. Serum IgG responses to heroin haptens coupled to TT 9 weeks after primary immunization. Mice were immunized with L(MPLA)+HerHap-TT (A) or L(MPLA)+OMAHap (B), L(MPLA)+MorHap (C), or L(MPLA)+6-AcMorHap (D) at 0 and 6 weeks. ELISA was conducted with the appropriate hapten coupled to BSA. Each curve represents an individual mouse (5 mice/liposome formulation). Values represent the mean±standard deviation of triplicate determinations. The grey line is an average of the 5 mice. Pre-immune sera were not elevated above assay background levels.
Figure 6:
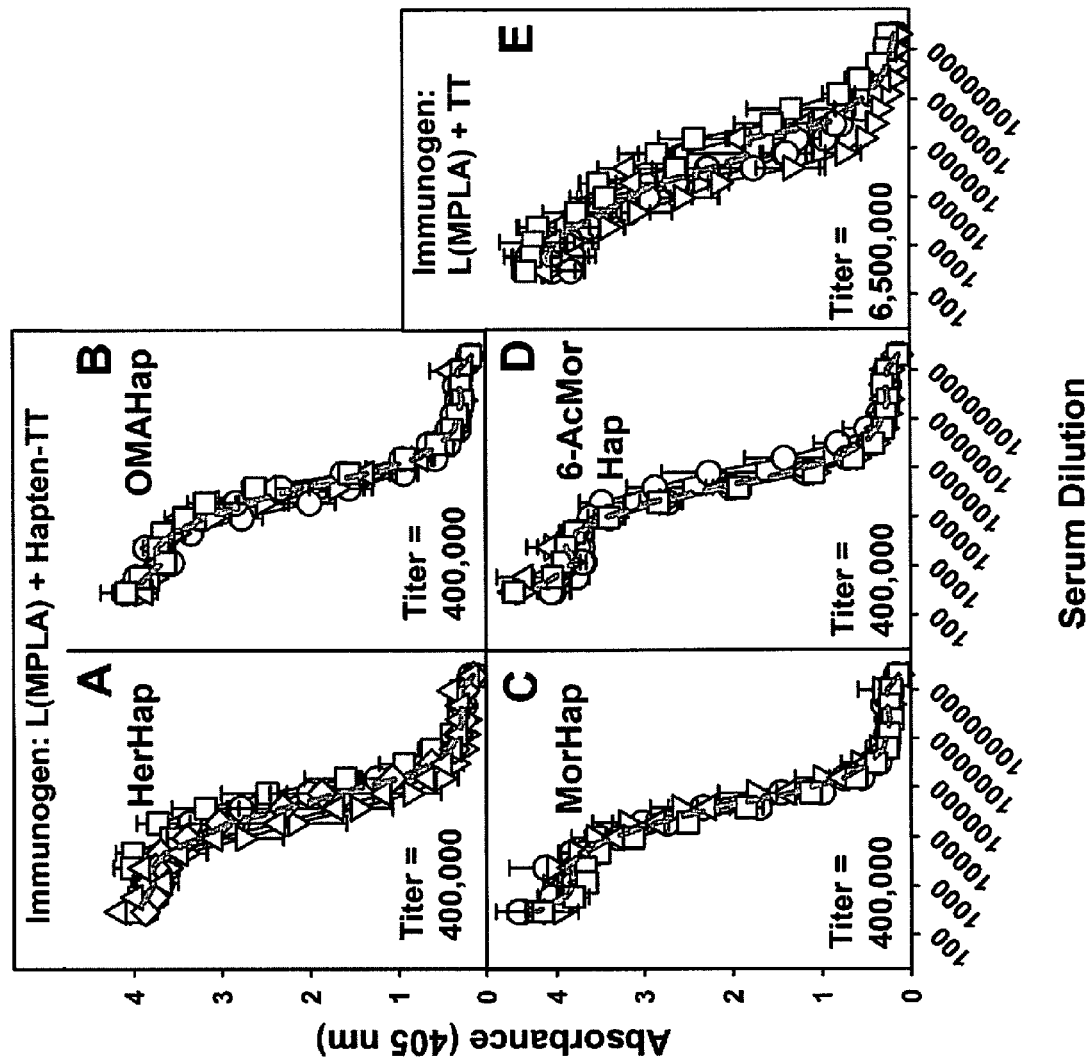
FIG. 6. Serum IgG responses to TT 9 weeks after primary immunization. Mice were immunized with L(MPLA+HerHap-TT) (A) or L(MPLA+OMAHap) (B), L(MPLA+MorHap) (C), L(MPLA+6-AcMorHap) (D), or L(MPLA)+TT (E) at 0 and 6 weeks. Each curve represents an individual mouse (5 mice/liposome formulation). Values represent the mean±standard deviation of triplicate determinations. The grey line is an average of the 5 mice. Pre-immune sera were not elevated above assay background levels.

Immune Response to Heroin Hapten-TT Carrier Mixed with Liposomes Containing MPLA Each of the haptens, HerHap, OMAHap, MorHap, and 6-AcMorHap, was conjugated to TT and mixed with liposomes containing MPLA. Although each of the conjugate formulations was highly immunogenic in mice, the relative respective anti-hapten titers observed differed greatly, with MorHap (6,500,000) (FIG. 5C)>HerHap (3,000,000) (FIG. 5A)>6-AcMorHap (500,000) (FIG. 5D)>OMAHap (100,000) (FIG. 5B). The relatively lower anti-hapten response of OMAHap-TT was consistent with the previously mentioned absence of anti-hapten antibodies observed after immunization with L(MPLA+OMAHap-PEG-MPER).

Remarkably, despite the above differing antibody titers to the different haptens conjugated to TT, with every conjugated hapten the immune response to the TT carrier was the same (400,000) (FIGS. 6A-D). However, as with the HerHap-MPER carrier formulations attached to liposomes containing MPLA (FIG. 4), the immune response to the hapten-free carrier itself [TT mixed with L(MPLA)] was much higher than to any of the TT conjugates (FIG. 6E). Thus, the conjugated hapten inhibited, but did not eliminate, the immune response to TT. The end result is that the titer to TT was greater than the titer to hapten after immunization with either 6-AcMorHap-TT or OMAHap-TT, but much lower than after immunization with MorHap-TT or HerHap-TT.

Discussion

The theoretical basis that underlies a potential vaccine against a haptenic drug such as nicotine, cocaine, methamphetamine, or an opiate (such as heroin or morphine), each of which drug has a receptor in the brain, is that specific antibodies to the drug will retard or block transmission of the drug across the blood-brain barrier (Janda K D, Treweek J B, 2011, Nat. Rev. Immunol. 12, 67-72; Shen et al., 2012, Clin. Pharmacol. Ther. 91, 60-70). The major challenge for such a vaccine, therefore, is to induce high titers of specific IgG antibodies that will block the drug, and this challenge is best addressed by using both a highly potent and safe adjuvant formulation and an appropriate hapten that is conjugated to a suitable carrier. In the present study we used liposomes containing MPLA as an adjuvant system, and four synthetic haptens were tested, HerHap, OMAHap, MorHap, and 6-AcMorHap, each of which might be used in a candidate vaccine to heroin.

Figure 7:
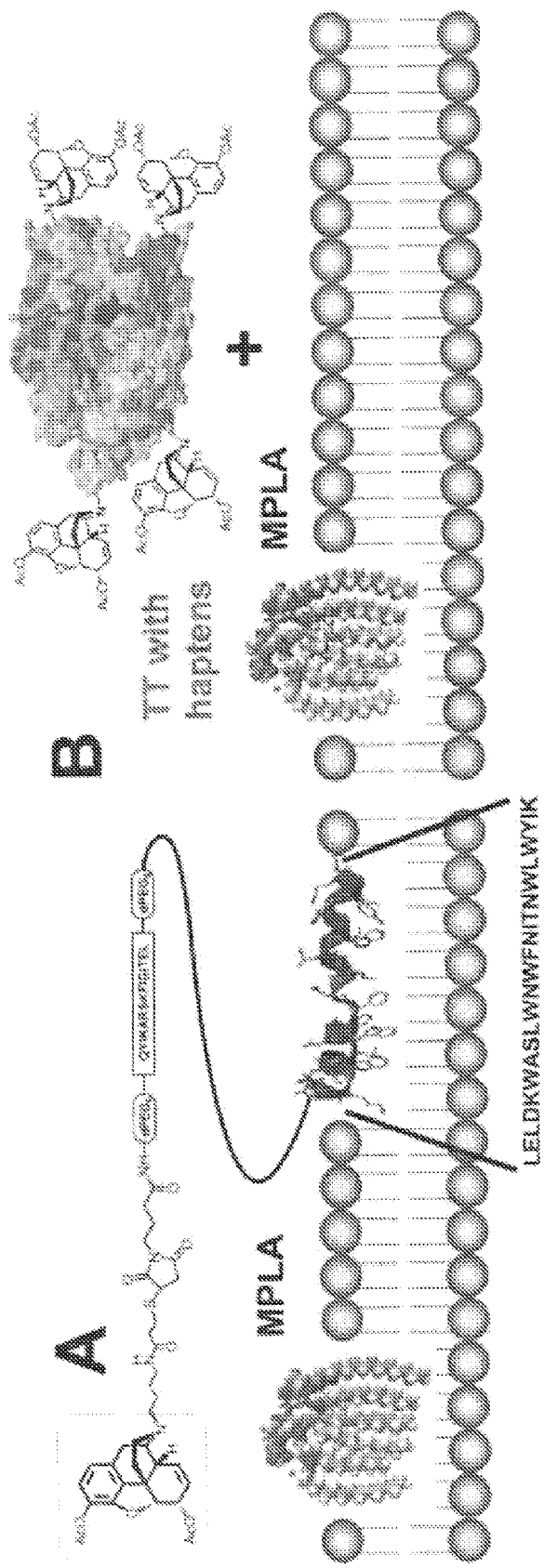
FIG. 7. Schematic illustrations of two hapten/adjuvant formulations used for immunization of mice to induce antibodies to heroin hapten. (A) L(MPLA) having surface-attached 23 amino acid MPER peptide to which the T helper peptide and heroin hapten were coupled. (B) Heroin hapten was coupled to TT and the coupled TT-hapten was mixed with L(MPLA) that served as an adjuvant. The entire TT was used for coupling with heroin hapten analogs, but for simplicity the graphic illustrates the 2.3 Å x-ray crystal structure of tetanus neurotoxin light chain, obtained from the RCSB Protein Data Bank (PDB ID: 1Z7H)(Breidenback M A, Brunger A T, 2005, Biochemistry 44:7450-7).

In this study two different carrier/adjuvant strategies for haptens were employed. In the first strategy, HerHap or OMAHap was conjugated to a hydrophobic carrier that contained a 23 amino acid MPER peptide that spontaneously associates with the outer surface of bilayers of liposomes containing MPLA during liposome formation (FIG. 7A). Under the conditions used this resulted in a mean titer of 12,800 to HerHap, but no detectable antibodies were induced to OMA-Hap. It is worth pointing out that the absence of an effect of liposomal sulfo-GalCer on the immunization with HerHap would not seem support the early suggestions that sulfo-GalCer might serve as an opiate binding site (Loh et al., 1974, supra; Loh et al., 1975, Life Sci. 16, 1811-1817; Loh et al., 1978, Fed. Proc. 37, 147-152; Farooqui and Horrocks, 1985, supra). However, after immunization of mice by using the second carrier-adjuvant strategy, in which each of the four haptens was directly conjugated to TT for immunization and each hapten conjugate was simply mixed with liposomes containing MPLA (FIG. 7B), even higher IgG endpoint titers of 6,500,000 for MorHap, 3,000,000 for HerHap, 500,000 for 6-AcMorHap, and 100,000 for OMAHap were observed.

Comparisons of titers obtained with various haptens, carriers, and adjuvants in other studies in the literature are complicated by the widespread use of "mid-point" titers (i.e., serum required for 50% of maximum absorbance in ELISA) (Stowe et al., 2011, J. Med. Chem. 54, 5195-5204; Anton et al., 2009, Hum. Vaccine 5, 214-229; Carrera et al., 2001, PNAS USA 98, 1988-1992; LeSage et al., 2006, Psychopharmacology 184, 409-416). With mid-point titers it is difficult to differentiate whether the plateau of absorbance in the ELISA is due to a plateau of substrate in the assay as opposed to an immunological plateau. Although titers obtained in mice and rats might differ because of species differences, in one study examination of the IgG titration curve of serum from rats 10 days after being immunized 4 times with a morphine/heroin hapten coupled to keyhole limpet hemocyanin with complete and incomplete Freund's adjuvant appeared to suggest an end point titer of approximately 100,000 (Li et al., 2011, J. Neurochem. 119, 1271-1281). Clearly, the down-selection of a hapten that would be most suitable for further testing for a candidate human vaccine to heroin would be dependent both on the titer and specificity of the induced antibodies based on affinity to heroin and its degradation products, and detailed studies of affinities are underway. We conclude from these results that liposomal MPLA can induce potent immune responses to heroin haptens, and liposomal MPLA might serve as a useful adjuvant system for inducing antibodies for a candidate opiate vaccine.

Interestingly, both HerHap and OMAHap blocked the induction of antibodies to the MPER peptide carrier, a highly immunogenic antigen when attached to liposomes containing MPLA. This observation was unexpected because according to immunological theory both the hapten itself and the carrier of the hapten should be immunogenic (Berzofsky J A, Verkower I J, Immunogenicity and antigen structure. In: Paul W E, editor. Fundamental Immunology, 6$^{th}$ Ed. Philadelphia: Lippincott-Raven; 2008, p. 631-683). It is possible that the conformation of the MPER peptide, sandwiched between the conjugated hapten and the outer surface of the liposomal membrane to which the MPER was attached precluded the appropriate display of the MPER as an antigen. Alternatively, some sort of immunological competition between the hapten and the MPER peptide might have occurred. Immunization of mice with each of the four hapten-TT conjugates using the second immunization strategy (FIG. 7B) also resulted in high titers (400,000) against the TT itself that were markedly less than the observed titer (6,500,000) after immunization of unconjugated TT was mixed with liposomes containing MPLA. Thus, it appears that competition or inhibition by the haptens and TT may have reduced the immune response to the TT carrier. Thus, in contrast to the results with MPER-carrier, hapten-TT conjugates induce high levels of antibodies against both the hapten and the carrier.

What is claimed is:

1. A hapten with a chemical formula chosen from the following:
    (i) N-((4R,4aR,7R,7aR,12bS)-9-hydroxy-3-methyl-2,3,4,4a,7,7a-hexahydro-1H-4,12-methanobenzofuro[3,2-e]isoquinolin-7-yl)-3-mercaptopropanamide;
    (ii) (4R,4aR,7S,7aR,12bS)-9-(3-mercaptopropanamido)-3-methyl-2,3,4,4a,5,6,7,7a-octahydro-1H-4,12-methanobenzofuro[3,2-e]isoquinolin-7-yl acetate;
    (iii) N,N'-((4R,4aR,7S,7aR,12bS)-3-(4-(3-mercaptopropanamido)butyl)-2,3,4,4a,5,6,7,7a-octahydro-1H-4,12-methanobenzofuro[3,2-e]isoquinoline-7,9-diyl)diacetamide;
    (iv) N-((4R,4aR,7S,7aR,12bS)-7-acetamido-3-methyl-2,3,4,4a,5,6,7,7a-octahydro-1H-4,12-methanobenzofuro[3,2-e]isoquinolin-9-yl)-3-mercaptopropanamide;
    (v) 3-mercapto-N-((4R,4aR,7R,7aS,12bS)-3-methyl-7-(2-oxopropyl)-2,3,4,4a,5,6,7,7a-octahydro-1H-4,12-methanobenzofuro[3,2-e]isoquinolin-9-yl)propanamide; and
    (vi) N-(4-((4R,4aR,7R,7aS,12bS)-7,9-bis(2-oxopropyl)-4,4a,5,6,7,7a-hexahydro-1H-4,12-methanobenzofuro[3,2-e]isoquinolin-3(2H)-yl)butyl)-3-mercaptopropanamide.

2. An immunoconjugate wherein a hapten of claim 1 is covalently linked to a carrier moeity.

3. An immunoconjugate comprising a hapten with a structural formula:
   N-((4R,4aS,7R,7aR,12bS)-4a,9-dihydroxy-3-methyl-2,3,4,4a,5,6,7,7a-octahydro-1H-4,12-methanobenzofuro[3,2-e]isoquinolin-7-yl)-3-mercaptopropanamide.

4. The immunoconjugate of claim 2 wherein the carrier moeity is any of MPER, tetanus toxin, KLH, and CRM.

5. The immunoconjugate of claim 4 wherein the MPER is a 23 amino acid peptide identified as SEQ ID NO:1.

6. The immunoconjugate of claim 5 wherein a 15 amino acid universal T cell epitope is used as a spacer, said epitope having a sequence identified as any of SEQ ID NO:2 and SEQ ID NO:3.

7. A composition comprising an immunologically effective amount of the immunoconjugate of claim 2 and a physiologically acceptable vehicle.

8. The composition of claim 7 further comprising an adjuvant.

9. The composition of claim 8 wherein the adjuvant is L(MPLA).

10. The composition of claim 9 wherein the immunoconjugate is embedded, associated or attached to L(MPLA).

11. A method for inducing an anti-heroin immune response in a subject comprising immunizing the subject with an immunologically effective amount of the composition of claim 7.

12. The method of claim 11 wherein the carrier is MPER or tetanus toxin.

13. A method for inducing an anti-heroin immune response without inducing an immune response to a carrier moiety in a subject comprising immunizing the subject with an immunologically effective amount of the composition of claim 10.

14. An antibody that binds the immunoconjugate of claim 2.

15. The antibody of claim 14, wherein the antibody binds heroin.

16. A composition comprising the antibody of claim 14 and a physiologically acceptable vehicle.

17. A vaccine composition comprising the immunoconjugate of claim 2.

18. The vaccine composition of claim 17 further comprising an adjuvant.

19. The vaccine composition of claim 18 wherein the adjuvant is L(MPLA).

20. The immunoconjugate of claim 3 wherein the hapten is covalently linked to a carrier moiety, wherein the carrier moeity is any of MPER, tetanus toxin, KLH, and CRM.

21. The immunoconjugate of claim 20 wherein the MPER is a 23 amino acid peptide identified as SEQ ID NO:1.

22. The immunoconjugate of claim 21 wherein a 15 amino acid universal T cell epitope is used as a spacer, said epitope having a sequence identified as any of SEQ ID NO:2 and SEQ ID NO:3.

23. A composition comprising an immunologically effective amount of the immunoconjugate of claim 3 and a physiologically acceptable vehicle.

24. The composition of claim 23 further comprising an adjuvant.

25. The composition of claim 24 wherein the adjuvant is L(MPLA).

26. The composition of claim 25 wherein the immunoconjugate is embedded, associated or attached to L(MPLA).

27. A method for inducing an anti-heroin immune response in a subject comprising immunizing the subject with an immunologically effective amount of the immunoconjugate composition of claim 23.

28. The method of claim 27 wherein the immunoconjugate composition further comprises a carrier, wherein said carrier is MPER or tetanus toxin.

29. A method for inducing an anti-heroin immune response without inducing an immune response to a carrier moiety in a subject comprising immunizing the subject with an immunologically effective amount of the composition of claim 26.

30. An antibody that binds the immunoconjugate of claim 3.

31. The antibody of claim 30, wherein the antibody binds heroin.

32. A composition comprising the antibody of claim 30 and a physiologically acceptable vehicle.

33. A vaccine composition comprising the immunoconjugate of claim 3.

34. The vaccine composition of claim 33 further comprising an adjuvant.

35. The vaccine composition of claim 34 wherein the adjuvant is L(MPLA).

* * * * *